United States Patent
Herrmann et al.

(10) Patent No.: US 8,241,681 B2
(45) Date of Patent: Aug. 14, 2012

(54) SYNERGISTIC MIXTURES OF BISABOLOL AND GINGER EXTRACT

(75) Inventors: Martina Herrmann, Einbeck (DE); Gabriele Vielhaber, Holzminden (DE); Imke Meyer, Bodenwerder (DE); Holger Joppe, Dassel (DE)

(73) Assignee: Symrise AG, Holzminden (DE)

( * ) Notice: Subject to any disclaimer, the term of this patent is extended or adjusted under 35 U.S.C. 154(b) by 572 days.

(21) Appl. No.: 12/090,041

(22) PCT Filed: Oct. 6, 2006

(86) PCT No.: PCT/EP2006/067130
§ 371 (c)(1),
(2), (4) Date: Aug. 11, 2008

(87) PCT Pub. No.: WO2007/042472
PCT Pub. Date: Apr. 19, 2007

(65) Prior Publication Data
US 2009/0220625 A1 Sep. 3, 2009

Related U.S. Application Data

(60) Provisional application No. 60/726,276, filed on Oct. 14, 2005.

(51) Int. Cl.
*A61K 36/71* (2006.01)
(52) U.S. Cl. ...................................... 424/756
(58) Field of Classification Search ................ None
See application file for complete search history.

(56) References Cited

U.S. PATENT DOCUMENTS

| 5,854,291 A | 12/1998 | Laughlin et al. |
| 6,391,346 B1 | 5/2002 | Newmark et al. |
| 2002/0136787 A1 | 9/2002 | Nitikhunkasem et al. |
| 2004/0116542 A1 | 6/2004 | Baumoeller et al. |

FOREIGN PATENT DOCUMENTS

| JP | 63033326 A | * | 2/1988 |
| WO | WO-03/075862 | | 9/2003 |
| WO | WO 2004091307 A2 | * | 10/2004 |

* cited by examiner

Primary Examiner — Amy L Clark
(74) Attorney, Agent, or Firm — Connolly Bove Lodge & Hutz LLP

(57) ABSTRACT

Described is a formulation having a skin irritation-reducing action consisting of or comprising: bisabolol and a composition or compound chosen from the group consisting of a) substance mixtures obtainable from an extraction of ginger, b) substance mixtures obtainable from a separation of a ginger extract which comprise a compound which is chosen from the group consisting of gingerols, shogaols, gingerdiols, dehydrogingerdiones, paradols and derivatives thereof and c) compounds obtainable from a separation of a ginger extract which are chosen from the group consisting of gingerols, shogaols, gingerdiols, dehydrogingerdiones, paradols and derivatives thereof and mixtures thereof, wherein the particular content of bisabolol and of the said composition or compound in the formulation is adjusted such that the skin irritation-reducing action of these contents is increased synergistically.

13 Claims, No Drawings

SYNERGISTIC MIXTURES OF BISABOLOL AND GINGER EXTRACT

The present invention relates to a formulation having a skin irritation-reducing action consisting of or comprising: bisabolol and a composition or compound chosen from the group consisting of
a) substance mixtures obtainable from an extraction of ginger,
b) substance mixtures obtainable from a separation of a ginger extract which comprise a compound which is chosen from the group consisting of gingerols, shogaols, gingerdiols, dehydrogingerdiones, paradols and derivatives thereof and
c) compounds obtainable from a separation of a ginger extract which are chosen from the group consisting of gingerols, shogaols, gingerdiols, dehydrogingerdiones, paradols and derivatives thereof
and mixtures thereof,
wherein the particular content of bisabolol and of the said composition or compound in the formulation is adjusted such that the skin irritation-reducing action of these contents is increased synergistically.

It also relates to a medicament for treatment of skin irritations and the use of such a formulation or of such a medicament for prophylaxis of skin irritation and/or treatment of skin irritations for medical and/or other than medical purposes.

It moreover relates to a process for the preparation of a formulation or of a medicament having a skin irritation-reducing action, a cosmetic or therapeutic method for prophylaxis and one for treatment of skin irritations, a method for prophylaxis of the skin-irritating action and a method for reducing, eliminating or suppressing the skin-irritating action of a substance or substance mixture and a kit comprising a formulation having a skin irritation-reducing action.

In the cosmetics and pharmaceuticals industry, there is a constant need for agents having a skin irritation-reducing action.

The skin, in particular the epidermis, as a barrier organ of the human organism is subjected to external influences to a particular extent. Many intrinsic (e.g. genetic predisposition) and extrinsic (e.g. damage to the skin barrier, action of UV light, irritating or allergy-inducing substances) factors can lead to skin irritation. In connection with this Application, skin irritation is to be understood as meaning any change to the skin which induces sensorial malaise in humans or animals and/or is characterized by a dry, reddened and/or inflamed skin symptoms. The term sensorial malaise here of course also includes states such as itching or pain. Skin irritation can include, in particular, phenomenologically different skin states: delicate skin, sensitive skin, including sensitive scalp, easily injured skin, atopic skin, irritated skin or inflamed skin, which manifests itself in an in each case higher severity in a reddening of the skin, so-called erythema.

The problem of "delicate skin" affects a growing number of adults and children. It is now assumed that up to 50% of the population have a delicate skin (L. Misery et al., Ann. Dermatol. Venereol. 2005, 132, 425-429). Delicate skin describes a skin having a reduced irritation threshold for irritants, such as hyper-reactive and intolerant, and also atopic skin. In the case of humans with delicate, sensitive or easily injured skin, a phenomenon called "stinging" ("to sting"=becoming injured, burn, be painful) can be observed. Typical adverse phenomena associated with the terms "stinging" or "sensitive skin" are reddening of the skin, tingling, prickling, tautness and burning of the skin and itching. They can be caused by stimulating environmental conditions, such as e.g. massage, action of surfactants, influence of weather, such as heat, cold, dryness and also damp heat, thermal radiation and UV radiation, e.g. from the sun, or psychological stress.

A "sensitive" scalp is likewise characterized by reddening of the skin, tingling, prickling, burning and itching. Triggers are, for example, soap, shampoos or other hair care compositions, surfactants, hard water having high lime concentrations and/or mechanical stress. Erythemas and hyperseborrhoea (excessive production of sebum) of the scalp and dandruff are often associated with the phenomena described.

In approx. 10-20% of the population of industrial countries, with an increasing trend, atopy is to be observed, a hypersensitivity, of familial origin, of the skin and mucous membranes to environmental substances with an increased readiness to develop hypersensitivity reactions of the immediate type (allergies) to substances from the natural environment. Atopy is presumed to be of genetic origin. Atopy can manifest itself as atopic dermatitis. In this case, the skin barrier is damaged and the skin is often inflamed and itches.

The erythematous action of the ultraviolet part of sunlight or artificial radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even more or less severe burns.

Erythematous skin symptoms also occur as concomitant symptoms with certain skin diseases or irregularities. For example, the typical skin rash of the symptoms of acne is regularly reddened to a greater or lesser degree and impairs the well-being of those affected even in mild cases.

Erythemas also occur to an increased extent in the nappy region of infants, and all the more so of babies (nappy dermatitis). Incontinence, a condition which occurs to an increased extent especially in old age, is also often associated with erythemas and reddening of the skin as a consequence of continual exposure to moisture and irritants (incontinence dermatitis).

A large number of active compounds having a skin irritation-reducing action are indeed already employed in the technical fields referred to, but alternatives nevertheless continue to be sought. In the connection of this text, skin irritation-reducing action is to be understood as meaning the moderation, reduction, elimination or prevention of skin irritations, in particular that of the skin symptoms described above. The skin irritation-reducing action here is based in particular on soothing of the skin, inhibition of inflammation and/or alleviation of reddening. In this text, the term "skin" also includes the term "mucous membrane". In the search for alternative agents, however, it should be remembered that the substances used must be toxicologically acceptable, tolerated well by the skin and stable (in particular in the conventional cosmetic and/or pharmaceutical formulations), should have the lowest possible intrinsic odour and the lowest possible intrinsic colour and must be inexpensive to prepare. In accordance with the persistent trend towards natural active compounds, novel active compounds of natural, in particular plant origin are sought in particular.

Persons skilled in the art have already addressed extensively the skin irritation-reducing properties of bisabolol and of ginger (*Zingiber officinale*) extract and the substances contained in it, such as gingerols, shogaols, gingerdiols, dehydrogingerdiones and paradols and derivatives thereof.

However, there was no indication hitherto that the mixtures of ginger extract or the compounds contained in this extract with bisabolol have, compared with the components used individually, a significantly improved, synergistic, skin irritation-reducing action. In the connection of this text, synergistic action is to be understood as meaning an action which is increased beyond the additive action of the compounds displaying synergy. This can be recorded by the synergy index (SI) value according to Kull (D. C. Steinberg, Cosmetics & Toiletries 2000, 115 (11), 59-62 and F. C. Kull et al., Applied Microbiology 1961, 9, 538-541). Substance combinations in which both components display the synergistically increased action, and also substance combinations in which only one component displays the synergistically increased action, while the other component acts merely as an intensifier (booster), fall under the given definition of the synergy effect. A synergistic combination of active compounds has the advantage that overall less active compound is required to achieve the particular action.

The skin irritation-reducing action of bisabolol is described in detail (e.g. H. Schilcher, Die Kamille: Handbuch für Ärzte, Apotheker u. a. Naturwissenschaftler [Camomile: Handbook for Doctors, Pharmacists and Other Scientists], Wissenschaftliche Verlagsgesellschaft, Stuttgart, 1987). However, studies on a synergistically increased activity in a combination of bisabolol with ginger extract or at least one of the active compounds contained in it, such as e.g. gingerols, shogaols, gingerdiols, dehydrogingerdiones and paradols and derivatives thereof, are not disclosed in any of the publications.

The skin irritation-reducing, in particular the antiinflammatory action of ginger (*Zingiber officinale*) extracts and the substances contained in them, in particular the gingerols, shogaols, gingerdiols, dehydrogingerdiones and paradols and derivatives thereof, is known (E. Tjendraputra et al., Bioorg. Chem. 2001, 29, 156-163; S. D. Jolad et al., Phytochem. 2004, 65, 1937-1954). However, studies of a synergistically increased activity in combination with bisabolol are disclosed neither in these nor in further publications.

The object of the present invention was therefore to provide a combination of components which has an improved skin irritation-reducing action.

This object is achieved by a formulation having a skin irritation-reducing action consisting of or comprising: bisabolol and a composition or compound chosen from the group consisting of
a) substance mixtures obtainable from an extraction of ginger,
b) substance mixtures obtainable from a separation of a ginger extract which comprise a compound which is chosen from the group consisting of gingerols, shogaols, gingerdiols, dehydrogingerdiones, paradols and derivatives thereof and
c) compounds obtainable from a separation of a ginger extract which are chosen from the group consisting of gingerols, shogaols, gingerdiols, dehydrogingerdiones, paradols and derivatives thereof
and mixtures thereof,
wherein the particular content of bisabolol and of the said composition or compound in the formulation is adjusted such that the skin irritation-reducing action of these contents is increased synergistically.

In view of the prior art, it was particularly surprising that the formulation according to the invention shows a highly synergistic activity and on e.g. skin irritated by detergent is significantly superior to individually dosed bisabolol or individually dosed ginger extract at the same concentration.

It has also been found that this synergistic activity of the reduction in skin irritation is not limited solely to acceleration of the subsidence ("repair") of the inflammation and/or reddening of the skin compared with untreated skin. Rather, the formulation according to the invention also has a highly synergistic action in reducing the development of erythema ("protection") e.g. due to detergents, UV irradiation or another of the abovementioned factors.

On the basis of the particularly significant increase in the action of its constituents, the formulation according to the invention is particularly suitable for reducing skin irritation, in particular for soothing the skin and/or inhibiting inflammation and/or reducing reddening, even at a low dosage of the formulation according to the invention.

For preparation of an effective synergistic formulation according to the invention comprising component (constituent) (A) and component (constituent) (B) which causes a particularly efficient reduction in skin irritation, it is sufficient to mix mixture constituent (B) with a small amount of constituent (A). In this context, component (A) is:
a) a ginger (*Zingiber officinale*) extract and/or
b) a substance mixture of the same composition as a ginger extract and/or
c) a substance mixture which is prepared from a separation of a ginger extract and comprises a compound which is chosen from the group consisting of gingerols, shogaols, gingerdiols, dehydrogingerdiones, paradols and derivatives thereof and/or
d) a compound which is prepared from a separation of a ginger extract and is chosen from the group consisting of gingerols, shogaols, gingerdiols, dehydrogingerdiones, paradols and derivatives thereof and/or
e) a substance mixture which is of the same composition as a substance mixture prepared from a separation of a ginger extract and comprises a compound which is chosen from the group consisting of gingerols, shogaols, gingerdiols, dehydrogingerdiones, paradols and derivatives thereof and/or
f) a compound such as can be prepared from a separation of a ginger extract, which is chosen from the group consisting of gingerols, shogaols, gingerdiols, dehydrogingerdiones, paradols and derivatives thereof,
and component (B) is: bisabolol.

Component (A) is very particularly preferably ginger extract, in particular ginger (*Zingiber officinale*) extract.

Preferably, the weight ratio of component (A) (preferably ginger extract) to bisabolol (B) is in the range of from 1:100, 000 to 1:10, preferably in the range of from 1:10,000 to 1:20, and particularly preferably in the range of from 1:1000 to 1:50.

Preferably, the sum of components (A) (preferably ginger extract) and (B) in a synergistic formulation according to the invention as the crude product is at least 90 wt. %, preferably at least 95 wt. %, particularly preferably at least 98 wt. %, based on the total weight of the formulation according to the invention.

Preferably, the amount of component (A) (preferably ginger extract) is in the range of 0.001-10 wt. %, particularly preferably in the range of 0.01-5 wt. %, in particular in the range of 0.1-2 wt. %, based on the total weight of the synergistic formulation according to the invention as the crude product and/or the content of component (B) is preferably 90-99.999 wt. %, particularly preferably 95-99.99 wt. %, in particular 98-99.9 wt. %, based on the total weight of the synergistic formulation according to the invention as the crude product.

The amount of component (A) (preferably ginger extract) and component (B) together in ready-to-use cosmetic formulations according to the invention is preferably 0.001-5 wt. %, particularly preferably 0.01-1 wt. %, in particular 0.01-0.25 wt. %, based on the total weight of the formulation. In the connection of this text, "ready-to-use" is to be understood as meaning that the formulation is intended for coming into contact with the skin in an unchanged form.

The bisabolol used in the context of the present invention can be of natural or synthetic origin, and is preferably "alpha-bisabolol". In the context of this text, the term "alpha-bisabolol" here includes (+)-alpha-bisabolol, (−)-alpha-bisabolol, (+)-epi-alpha-bisabolol and (−)-epi-alpha-bisabolol and mixtures of two, three or all of the isomers of alpha-bisabolol mentioned. In particular, the term "alpha-bisabolol" includes racemic mixtures of (+/−)-alpha-bisabolol and/or (+/−)-epi-alpha-bisabolol. Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

Component A employed for preparation of the formulation according to the invention is, in the case of ginger extract (also as a precursor), preferably extracts of the fresh or dried ginger root which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols. Essential ginger oils, obtained by steam distillation, are not suitable as a constituent in the context of the synergistic formulations according to the invention due to the absence of constituents such as e.g. gingerols, shogaols, gingerdiols, dehydrogingerdiones and/or paradols.

For the separation of a ginger extract for the preparation of component (A), it is not difficult for the person skilled in the art to choose suitable separation methods known from the prior art. The person skilled in the art can also choose suitable processes from the prior art for the preparation of "synthetic" ginger extracts (that is to say substance mixtures which correspond to ginger extracts in their composition but have not been obtained by extraction from ginger. The same also applies to substance mixtures and compounds which are obtainable from a separation of a ginger extract but have been prepared in another manner than by separation of a ginger extract.

A formulation according to the invention having a skin irritation-reducing action wherein the contents of component (A) and of component (B) in each case have a skin irritation-reducing action is preferred. The advantage of the preferred formulation according to the invention lies in the fact that they reduce skin irritations particularly effectively.

The invention also provides a medicament for treatment of skin irritations, comprising or consisting of a formulation according to the invention having an irritation-reducing action. Such a medicament can be employed in the field of human and veterinary medicine against a large number of diseases, such as, for example, urticaria, contact dermatitis, atopy and generally all inflammation processes, included tooth and gum inflammations, such as parodontosis.

A formulation according to the invention can be further processed to a formulation according to the invention in solid form by optionally adding a pharmaceutically and/or cosmetically acceptable solid carrier to the formulation and then drying the mixture by suitable processes. In this context, such a solid which is at least not toxic to the organisms on which it is to be used is pharmaceutically or cosmetically acceptable.

The formulation according to the invention can also be further processed to a diluted formulation according to the invention in liquid form by optionally adding a pharmaceutically and/or cosmetically acceptable solvent, such as e.g. neutral oil, mineral oil, silicone oil, plant oils, fatty alcohols, fatty acid esters, ethanol, 1,2-propylene glycol, 1,3-butylene glycol, 1,2-pentanediol and water and mixtures of two or more of the solvents mentioned, to the mixture. Such formulations prepared according to the invention are readily further processable in particular for cosmetic purposes. These formulations according to the invention can optionally be prepared with the addition of a solubilizing agent, preservative or antioxidant, such as, for example, the Extrapon Ginger obtainable from Symrise employed in Example 11.

The formulation according to the invention or the liquid or solid formulation comprising the formulation can furthermore also be further processed by encapsulation. According to the invention, the formulation according to the invention and/or the liquid or solid formulation comprising this is encapsulated with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of the substances mentioned.

Essential fields of use for formulations according to the invention are cosmetic, in particular dermatological formulations which (apart from the presence of the synergistic formulation according to the invention) have the conventional composition and serve for cosmetic, in particular dermatological light protection, for treatment, care and cleansing of the skin and/or hair or as a make-up product in decorative cosmetics. Such formulations can accordingly be present e.g. as a cleansing composition, such as e.g. soap, syndet, liquid washing, shower and bath preparation, skin care composition, such as e.g. emulsion (as a solution, dispersion, suspension; cream, lotion or milk of the W/O, O/W or multiple emulsion, PIT emulsion, emulsion foam, micro-, nanoemulsion, Pickering emulsion type, depending on the preparation process and constituents), ointment, paste, gel (including hydro-, hydrodispersion-, oleogel), alcoholic or aqueous/alcoholic solution, oil, toner, balsam, serum, powder, wipe, Eau de Toilette, Eau de Cologne, perfume, wax, including the presentation form as a stick, roll-on, (pump) spray, aerosol (foaming, non-foaming or after-foaming), skin care composition (as described above) as a foot care composition (including keratolytics, deodorant), as an insect repellent composition, as a sunscreen composition, as a self-tanning composition and/or aftersun preparation, skin care composition as a shaving composition or after-shave, as a hair-removing composition, as a hair care composition, such as e.g. shampoo (including shampoo for normal hair, for greasy hair, for dry, stressed (damaged) hair, 2-in-1 shampoo, anti-dandruff shampoo, baby shampoo, shampoo for a dry scalp, shampoo concentrate), conditioner, hair treatment course, hair lotion, hair rinse, styling cream, pomade, permanent wave and fixing compositions, hair smoothing composition (straightening composition, relaxer), hair setting composition, styling aid (e.g. gel or wax); blonding composition, hair colouring composition, such as e.g. temporary, directly absorbed, semi-permanent hair colouring composition, permanent hair colouring composition), skin care composition as a decorative body care composition, such as e.g. nail care composition (nail varnish and nail varnish remover), decorative cosmetic (e.g. powder, eye shadow, kajal pencil, lipstick), skin care composition as a deodorant and/or antiperspirant; mouthwash and mouth spray.

A further aspect of the present invention relates to formulations according to the invention in the form of oral care products (oral hygiene products), wherein the oral care product is preferably in the form of toothpaste, dental cream, dental gel, dental powder, tooth-cleaning liquid, tooth-cleaning foam, mouthwash, dental cream and mouthwash as a 2-in-1 product, sweet for sucking, mouth spray, dental silk or dental care chewing gum. The activity of the formulations according to the invention also manifests itself remarkably well in the field of oral hygiene. A bad breath-reducing activity of the formulations according to the invention has moreover been found in our own studies.

Dental care compositions (as a preferred example of an oral care product according to the invention) in general comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, aromas, sodium bicarbonate and/or odour correctants.

Formulations according to the invention in the form of chewing gums or dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases comprise further constituents, such as, for example, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations according to the invention (in particular those which are in the form of an oral care product) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, ginger oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the formulations according to the invention comprise at least one aroma substance, preferably 2, 3, 4, 5, 6, 7, 8, 9, 10 or more aroma substances, chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Preferred cooling active compounds for use in formulations according to the invention are listed in the following. The person skilled in the art can supplement the following list with a large number of further cooling active compounds; the cooling active compounds can also be employed in combination with one another. Preferably, the formulations according to the invention comprise at least one cooling active compound, preferably two or more cooling active compounds, chosen from the group consisting of:

menthone glycerol acetal (trade name: Frescolat®MGA, Symrise GmbH & Co. KG, Germany), menthyl lactate (trade name: Frescolat®ML, Symrise GmbH & Co. KG, Germany, menthyl lactate is preferably I-menthyl lactate, in particular I-menthyl I-lactate), substituted menthyl-3-carboxylic acid amides (e.g. menthyl-3-carboxylic acid N-ethylamide, also known as WS-3), 2-isopropyl-N-2,3-trimethylbutanamide (also known as WS-23), substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin.

Particularly preferred cooling active compounds are: menthone glycerol acetal (trade name: Frescolat®MGA), menthyl lactate (preferably I-menthyl lactate, in particular I-menthyl I-lactate, trade name: Frescolat®ML), substituted menthyl-3-carboxylic acid amides (e.g. menthyl-3-carboxylic acid N-ethylamide), 2-isopropyl-N-2,3-trimethylbutanamide, 3-menthoxypropane-1,2-diol, 2-hydroxyethyl menthyl carbonate, 2-hydroxypropyl menthyl carbonate, isopulegol and monomenthyl succinate.

Formulations according to the invention which comprise I-menthol and at least one, particularly preferably at least two cooling substances are preferred according to the invention.

Preferably, a formulation according to the invention comprises a mixture of flavouring and/or aroma substances which imparts to a formulation according to the invention an overall herbal (herb-like), minty, cinnamon-like, clove-like, wintergreen and/or fruity character.

The (in particular topical) cosmetic or pharmaceutical formulations according to the invention can comprise cosmetic auxiliary substances and additives such as are conventionally used in such formulations, e.g. sunscreen agents, preservatives, bactericides, fungicides, virucides, cooling active compounds, insect repellents (e.g. DEET, IR 3225), plant extracts, plant parts, antiinflammatory active compounds, substances which accelerate wound healing (e.g. chitin or chitosan and derivatives thereof), film-forming substances (e.g. polyvinylpyrrolidones or chitosan or derivatives thereof), antioxidants, vitamins, 2-hydroxycarboxylic acids (e.g. citric acid, malic acid, L-, D- or dl-lactic acid), skin-colouring agents (e.g. walnut extracts or dihydroxyacetone), active compounds for promoting hair growth or inhibiting hair growth, skin care compositions (e.g. cholesterol, ceramides, pseuodceramides), softening, moisturizing and/or humectant substances, fats, oils, saturated fatty acids, mono- or polyunsaturated fatty acids, α-hydroxy acids, polyhydroxy-fatty acids or derivatives thereof, waxes or other conventional constituents of a cosmetic or dermatological formulation, such as alcohols, polyols, polymers, foam stabilizers, electrolytes, organic solvents, silicone derivatives of chelating agents (e.g. ethylenediaminetetraacetic acid and derivatives), antidandruff active compounds (e.g. climbazole, ketoconazole, piroctonoleamine, zinc pyrithione), hair care agents, perfumes, substances for preventing foaming, dyestuffs, pigments which have a colouring action, thickening agents (advantageously silicon dioxide, aluminium silicates, such as e.g. bentonites, polysaccharides or derivatives thereof, e.g. hyaluronic acid, guar bean flour, xanthan gum, hydroxypropylmethylcellulose or allulose derivatives, particularly advantageously polyacrylates, such as e.g. Carbopols or polyurethanes), surface-active substances and emulsifiers.

The particular amounts of cosmetic (optionally dermatological) auxiliary substances and additives and perfume to be employed can be easily determined according to the nature of the particular product by simple trials by the person skilled in the art.

The formulations according to the invention can also preferably comprise further skin irritation-reducing active compounds. In this case, all the skin irritation-reducing active compounds which are suitable or usual for cosmetic and/or dermatological uses can be used in this respect. Steroidal antiinflammatory substances of the corticosteroid type are advantageously employed for this, such as e.g. hydrocortisone, hydrocortisone derivatives, such as hydrocortisone 17-butyrate, dexamethasone, dexamethasone phosphate, methylprednisolone or cortisone, it being possible for the list to be extended by addition of further steroidal antiinflammatories. Non-steroidal antiinflammatories can also be employed. There are to be mentioned here by way of example oxicams, such as piroxicam or tenoxicam; salicylates, such as aspirin, Disalcid, Solprin or fendosal; acetic acid derivatives, such as diclofenac, fenclofenac, indomethacin, sulindac, tolmetin or clindanac; fenamates, such as mefenamic, meclofenamic, flufenamic or niflumic; propionic acid derivatives, such as ibuprofen, naproxen or benoxaprofen, or pyrazoles, such as phenylbutazone, oxyphenylbutazone, febrazone or azapropazone. Alternatively, natural antiinflammatory substances or reddening- and/or itching-alleviating substances can be employed. Plant extracts, specific highly active plant extract fractions and highly pure active substances isolated from plant extracts, can be employed. Extracts, fractions and active substances from aloe vera, *Commiphora* species, *Rubia* species, willow, rose-bay willow-herb, oats, calendula, arnica, St. John's wort, honeysuckle, rosemary, *Melissa, Passiflora incarnata*, witch hazel, *Pueraria, Dianthus* or *Echinacea*, as well as pure substances, such as, inter alia, apigenin, apigenin 7-glucoside, rosemary acid, boswellic acid, phytosterols, glycyrrhizic acid, glabridin, licochalcone A and anthranilic acid amides, such as, in particular, avenanthramides or dianthramides, are particularly preferred.

The amount of antiirritants (one or more compounds) in the formulations is preferably 0.0001 to 20 wt. %, particularly preferably 0.0001-10 wt. %, in particular 0.001-5 wt. %, based on the total weight of the formulation.

The formulations according to the invention can also comprise antioxidants, it being possible for all the antioxidants which are suitable or usual for cosmetic and/or dermatological uses to be used. The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), (metal) chelators, e.g. α-hydroxy-fatty acids, palmitic acid, phytic acid, lactoferrin, α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glycosides, such as e.g. 6-O-acyl-2-O-α-D-glucopyranosyl-L- ascorbic acid, 6-O-acyl-2-O-β-D-glucopyranosyl-L-ascorbic acid, 2-O-α-D-glucopyranosyl-L-ascorbic acid or 2-O-β-D-glucopyranosyl-L-ascorbic acid), tocopherols and derivatives thereof (e.g. vitamin E acetate), vitamin A and derivatives thereof (vitamin A palmitate) as well as coniferylbenzoate of benzoin resin, rutic acid and derivatives thereof, α-glucosylrutin, quercetin and derivatives thereof, rosemary acid, carnosol, carnosol acid, resveratrol, caffeic acid and derivatives thereof, sinapic acid and derivatives thereof, ferulic acid and derivatives thereof, furfurylideneglucitol, curcuminoids, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and derivatives (salts, esters, ethers, sugars, nucleotides, nucleosides, peptides and lipids) of these active compounds mentioned or antioxidatively active extracts or fractions from plants, such as e.g. green tea, rooibos, honeybush, grape, rosemary, sage, *Melissa*, thyme, lavender, olive, oats, cocoa, ginkgo, ginseng, liquorice, honeysuckle, *Sophora, Pueraria, Pinus, Citrus, Phyllanthus emblica* or St. John's wort.

The amount of antioxidants (one or more compounds) in the formulations according to the invention is preferably 0.01 to 20 wt. %, particularly preferably 0.05 to 10 wt. %, in particular 0.2-5 wt. %, based on the total weight of the formulation.

The formulations according to the invention advantageously comprise at least one UVA filter and/or at least one UVB filter and/or at least one inorganic pigment. In this context, the formulations can be in various forms such as are conventionally employed e.g. for sunscreen formulations for protecting the skin and hair against ultraviolet radiation. They can thus form e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol. In this context, the total amount of filter substances is from 0.01 wt. % to 40 wt. %, preferably 0.1 to 10 wt. %, in particular 1.0 to 5.0 wt. %, based on the total weight of the formulations.

Advantageous UV filters are e.g.: p-aminobenzoic acid, p-aminobenzoic acid ethyl ester (25 mol) ethoxylated, p-dimethylaminobenzoic acid 2-ethylhexyl ester, p-aminobenzoic acid ethyl ester (2 mol) N-propoxylated, p-aminobenzoic acid glycerol ester, salicylic acid homomethyl ester (homosalate) (Neo Heliopan®HMS), salicylic acid 2-ethylhexyl ester (Neo Heliopan®OS), triethanolamine salicylate, 4-isopropylbenzyl salicylate, anthranilic acid menthyl ester (Neo Heliopan®MA), diisopropylcinnamic acid ethyl ester, p-methoxycinnamic acid 2-ethylhexyl ester (Neo Heliopan®AV), diisopropylcinnamic acid methyl ester, p-methoxycinnamic acid isoamyl ester (Neo Heliopan®E 1000), p-methoxycinnamic acid diethanolamine salt, p-methoxycinnamic acid isopropyl ester, 2-ethylhexyl 2-cyano-3,3-diphenylacrylate (Neo Heliopan®303), ethyl 2-cyano-3,3'-diphenylacrylate, 2-phenylbenzimidazolsulfonic acid and salts (Neo Heliopan®Hydro), 3-(4'-trimethylammonium)-benzylidene-bornan-2-one methyl-sulfate, terephthalylidene-dibornanesulfonic acid and salts (Mexoryl®SX), 4-t-butyl-4'-methoxy-dibenzoylmethane (avobenzone)/(Neo Heliopan®357), β-Imidazole-4(5)-acrylic acid (urocanic acid), 2-hydroxy-4-methoxybenzophenone (Neo Heliopan®BB), 2-hydroxy-4-methoxybenzophenone-5-sulfonic acid, dihydroxy-4-methoxybenzophenone, 2,4-dihydroxybenzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methylbenzophenone, 3-(4'-sulfo)benzylidene-bornan-2-one and salts, 3-(4'-methylbenzylidene)-d,l-camphor (Neo Heliopan®MBC), 3-benzylidene-d,l-camphor, 4-isopropyldibenzoylmethane, 2,4,6-trianilino-(p-carbo-2'-ethylhexyl-1'-oxy)-1,3,5-triazine, phenylene-bis-benzimidazyl-tetrasulfonic acid disodium salt (Neo Heliopan®AP), 2,2'-(1,4-phenylene)-bis-(1H-benzimidazole-4,6-disulfonic acid), monosodium salt, N-[(2 and 4)-[2-(oxoborn-3-ylidene)methyl]benzyl]-acrylamide polymer, phenol, -(2H-benzotriazol-2-yl)-4-methyl-6-(2-methyl-3(1,3,3,3-tetramethyl-1-(trimethylsilyl)-oxy)-disiloxyanyl)-propyl), (Mexoryl®XL), 4,4'-[(6-[4-(1,1-dimethyl)-aminocarbonyl]-phenylamino]-1,3,5-triazine-2,4-diyl)diimino]-bis-(benzoic acid 2-ethylhexyl ester) (Uvasorb®HEB), 2,2'-methylene-bis-(6-(2H-benzotriazol-2-yl)-4-(1,1,3,3-tetramethylbutyl)-phenol), (Tinosorb®M), 2,4-bis-[4-(2-ethyl hexyloxy)-2-hydroxyphenyl]-1,3,5-triazine, benzylidene malonate-polysiloxane (Parsol®SLX), glyceryl ethylhexanoate dimethoxycinnamate, disodium 2,2'-dihydroxy-4,4'-dimethoxy-5,5'-disulfo-benzophenone, dipropylene glycol salicylate, sodium hydroxymethoxybenzophenone-sulfonate, 4,4',4-(1,3,5-triazine-2,4,6-triyltriimino)-tris-benzoic acid tris(2-ethylhexyl ester) (Uvinul®T150), 2,4-bis-[{(4-(2-ethyl-hexyloxy)-2-hydroxy}-phenyl]-6-(4-methoxyphenyl)-1,3,5-triazine, (Tinosorb®S),2,4-bis-[{(4-(3-sulfonato)-2-hydroxy-propyloxy)-2-hydroxy}-phenyl]-6-(4-methoxyphenyl)-1,3,5-triazine sodium salt, 2,4-bis-[{(3-(2-propyloxy)-2-hydroxy-propyloxy)-2-hydroxy}-phenyl]-6-(4-methoxy-phenyl)-1,3,5-triazine, 2,4-bis-[{4-(2-ethyl-hexyloxy)-2-hydroxy}-phenyl]-6-[4-(2-methoxyethyl-carbonyl)-phenylamino]-1,3,5-triazine, 2,4-bis-[{4-(3-(2-propyloxy)-2-hydroxy-propyloxy)-2-hydroxy}-phenyl]-6-[4-(2-ethylcarboxyl)-phenylamino]-1,3,5-triazine, 2,4-bis-[{4-(2-ethyl-hexyloxy)-2-hydroxy}-phenyl]-6-(1-methyl-pyrrol-2-yl)-1,3,5-triazine, 2,4-bis-[{4-tris-(trimethylsiloxy-silylpropyloxy)-2-hydroxy}-phenyl]-6-(4-methoxyphenyl)-1,3,5-triazine, 2,4-bis-[{4-(2"-methylpropenyloxy)-2-hydroxy}-phenyl]-6-(4-methoxyphenyl)-1,3,5-triazine, 2,4-bis-[{4-(1',1',1',3',5',5',5'-heptamethylsiloxy-2"-methyl-propyloxy)-2-hydroxy}-phenyl]-6-(4-methoxyphenyl)-1,3,5-triazine, 2-(4-diethylamino-2-hydroxybenzoyl)-benzoic acid hexyl ester (Uvinul® A Plus) and indanylidene compounds according to DE 100 55 940 (=WO 02/38537).

In this context, UV absorbers which are particularly suitable for combination are p-aminobenzoic acid, 3-(4'-trimethylammonium)-benzylidene-bornan-2-one methyl-sulfate, salicylic acid homomethyl ester (Neo Heliopan®HMS), 2-hydroxy-4-methoxy-benzophenone (Neo Heliopan®BB), 2-phenylbenzimidazolsulfonic acid (Neo Heliopan®Hydro), terephthalylidene-dibornanesulfonic acid and salts (Mexoryl®SX), 4-tert-butyl-4'-methoxydibenzoylmethane (Neo Heliopan®357), 3-(4'-sulfo)benzylidene-bornan-2-one and salts, 2-ethylhexyl 2-cyano-3,3-diphenylacrylate (Neo Heliopan®303), N-[(2 and 4)-[2-(oxoborn-3-ylidene)methyl]benzyl]-acrylamide polymer, p-methoxycinnamic acid 2-ethylhexyl ester (Neo Heliopan®AV), p-aminobenzoic acid ethyl ester (25 mol) ethoxylated, p-methoxycinnamic acid isoamyl ester (Neo Heliopan®E 1000), 2,4,6-trianilino-(p-carbo-2'-ethylhexyl-1'-oxy)-1,3,5-triazine (Uvinul®T150), phenol, 2-(2H-benzotriazol-2-yl)-4-methyl-6-(2-methyl-3(1,3,3,3-tetramethyl-1-(trimethylsilyl)-oxy)-disiloxyanyl)-propyl), (Mexoryl®XL), 4,4'-[(6-[4-(1,1-dimethyl)-aminocarbonyl]-phenylamino]-1,3,5-triazine-2,4-diyl)-diimino]-bis-(benzoic acid 2-ethylhexyl ester), (UvasorbHEB), 3-(4'-methylbenzylidene)-d,l-camphor (Neo Heliopan®MBC), 3-benzylidenecamphor, salicylic acid 2-ethylhexyl ester (Neo Heliopan®OS),4-dimethylaminobenzoic acid 2-ethylhexyl ester (Padimate O), hydroxy-4-methoxy-benzophenone-5-sulfonic acid and Na salt, 2,2'-methylene-bis-(6-(2H-benzotriazol-2-yl)-4-(1,1,3,3-tetramethylbutyl)-phenol), (Tinosorb®M), phenylene-bis-benzimidazyl-tetrasulfonic acid disodium salt (Neo Heliopan®AP), 2,4-bis-[{(4-(2-ethyl-hexyloxy)-2-hydroxy}-phenyl]-6-(4-methoxyphenyl)-1,3,5-triazine, (Tinosorb®S), benzylidene malonate-polysiloxane (Parsol®SLX), menthyl anthranilate (Neo Heliopan®MA), 2-(4-diethylamino-2-hydroxybenzoyl)-benzoic acid hexyl ester (Uvinul® A Plus) and indanylidene compounds according to DE 100 55 940 (=WO 02/38537).

Advantageous inorganic sunscreen pigments are finely disperse metal oxides and metal salts, for example titanium dioxides, zinc oxide (ZnO), iron oxides (e.g. $Fe_2O_3$), aluminium oxide ($Al_2O_3$); cerium oxides (e.g. $Ce_2O_3$), manganese oxides (e.g. MnO), zirconium oxide ($ZrO_2$), silicon oxide ($SiO_2$), mixed oxides of the corresponding metals and mixtures of such oxides, barium sulfate and zinc stearate. They are particularly preferably pigments based on $TiO_2$ or zinc oxide. In preferred embodiments, the particles have an average diameter of less than 100 nm, preferably between 5 and 50 nm and particularly preferably between 15 and 30 nm. They can have a spherical shape, but those particles which have an ellipsoid shape or a shape which deviates otherwise from the spherical can also be employed. The pigments can also be in a form treated on the surface, i.e. hydrophilized or hydrophobized. Typical examples are coated titanium dioxides, such as e.g. titanium dioxide T 805 (Degussa) or Eusolex® T2000 (Merck), or coated zinc oxide, such as e.g. Zinc Oxide NDM. In this context, possible hydrophobic coating agents are, above all, silicones, and in this case specifically trialkoxyoctysilanes or simethicone. So-called micro- or nanopigments are preferably employed in sunscreen compositions. Zinc micro- or nanopigments are preferably employed.

The total amount of inorganic pigments, in particular hydrophobic inorganic micropigments, in the finished cosmetic or dermatological formulations is advantageously in the range of from 0.1 to 30 wt. %, preferably 0.1 to 10.0, in particular 0.5 to 6.0 wt. %, based on the total weight of the formulations.

Cosmetic formulations according to the invention which comprise a formulation according to the invention having a skin irritation-reducing action can also comprise active compounds and active compound combinations against ageing of the skin and wrinkles. According to the invention, all the active compounds against ageing of the skin and wrinkles which are suitable or usual for cosmetic and/or dermatological uses can be used here. Advantageous active compounds against ageing of the skin and wrinkles in this respect are soya protein or protein hydrolysates, soya isoflavones, hydrolyzed rice protein, hydrolysed hazelnut protein, oligopeptides from hydrolysed Hibiscus esculentus extract, wheat protein, β-glucans, e.g. from oats, and derivatives thereof, glycoproteins, ursolic acid and its salts, betulin, betulic acid and its salts, retinol, retinol palmitate, propyl gallate, precocenes, 6-hydroxy-7-methoxy-2,2-dimethyl-1 (2H)-benzopyran, 3,4-dihydro-6-hydroxy-7-methoxy-2,2-di methyl-1 (2H)-benzopyran, creatine or other synthetic or natural active compounds against ageing of the skin and wrinkles, it being possible for the latter also to be used in the form of an extract from plants, such as e.g. green tea, *Rubus fruticosus*, *Sanguisorba officinalis*, *Centella asiatica*, *Ribes nigrum*, *Passiflora incarnata*, *Filipendula ulmaria*, *Phyllanthus emblica*, *Potentilla* species, okra, algae, evening primrose, pomegranate, lady's mantle, rosemary, sage, *Echinacea*, birch, apple or soya.

Substances which are particularly preferred for use as further active compounds against ageing of the skin are β-glucans, and 1,3-1,4-linked β-glucan from oats, *Rubus fruticosus* extract or wheat protein is particularly preferred.

Preferably, the formulations according to the invention can also comprise active compounds which stimulate shading or browning of the skin and hair in a chemical or natural manner. A faster action based on synergistic effects is thereby achieved. Substances which are particularly preferred in this context are substrates or substrate analogues of tyrosinase, such as L-tyrosine, L-DOPA or L-dihydroxyphenylalanine, stimulators of tyrosinase activity or expression, such as theophylline, caffeine, propiomelanocortin peptides, such as ACTH, alpha-MSH, peptide analogues thereof and other substances which bind to the melanocortin receptor, peptides, such as Val-Gly-Val-Ala-Pro-Gly, Lys-Ile-Gly-Arg-Lys or Leu-Ile-Gly-Lys, purines, pyrimidines, folic acid, copper salts, such as copper gluconate, chloride or pyrrolidonate, flavonoids, flavanone glycosides, such as naringin and hesperidin, melanin derivatives, such as Melasyn-100 and MelanZe, diacylglycerols, aliphatic or cyclic diols, psoralene, prostaglandins and analogues thereof, activators of adenylate cyclase and compounds which activate the transfer of melanosomes into keratinocytes, such as serine proteases or agonists of the PAR-2 receptor, extracts from plants and plant parts of the *Chrysanthemum* species or *Sanguisorba* species, walnut extracts, urucum extracts, rhubarb extracts, erytrulose and dihydroxyacetone.

The formulations according to the invention can also be employed in combination with skin-lightening active compounds. According to the invention, all the skin-lightening active compounds which are suitable or usual for cosmetic and/or dermatological uses can be used here. Advantageous skin-lightening active compounds in this respect are kojic acid (5-hydroxy-2-hydroxymethyl-4-pyranone), kojic acid derivatives, such as e.g. kojic acid dipalmitate, arbutin, ascorbic acid, ascorbic acid derivatives, hydroquinone, hydroquinone derivatives, resorcinol, sulfur-containing molecules, such as e.g. cysteine, alpha-hydroxy acids (e.g. citric acid, lactic acid, malic acid) and derivatives thereof, N-acetyl-tyrosine and derivatives, undecenoylphenylalanine, gluconic acid, 4-alkylresorcinols, 4-(1-phenylethyl)-1,3-benzenediol, chromone derivatives, such as aloesin, flavonoids, thymol derivatives, 1-aminoethylphosphinic acid, thiourea derivatives, ellagic acid, nicotinamide, zinc salts, such as e.g. zinc chloride or gluconate, thujaplicin and derivatives, triterpenes, such as maslic acid, sterols, such as ergosterol, benzofuranones, such as senkyunolide, vinyl- and ethylguaiacol, inhibitors of nitrogen oxide synthesis, such as e.g. L-nitroarginine and derivatives thereof, 2,7-dinitroindazole or thiocitrullin, metal chelators (e.g. α-hydroxy-fatty acids, palmitic acid, phytic acid, lactoferrin, humic acid, bile acid, bile extracts, bilirubin, biliverdin, EDTA, EGTA and derivatives thereof), retinoids, soya milk, serine protease inhibitors or liponic acid or other synthetic or natural active compounds for lightening of the skin and hair, the latter also being used in the form of an extract from plants, such as e.g. bearberry extract, rice extract, liquorice root extract or constituents concentrated therefrom, such as glabridin or licochalcone A, *Artocarpus* extract, extract from *Rumex* and *Ramulus* species, extracts from pine species (*Pinus*) and extracts from *Vitis* species or stilbene derivatives concentrated therefrom, and extract from *Saxifraga*, mulberry, *Scutellaria* or/and grape.

Formulations according to the invention can advantageously also comprise moisture retention regulators. The following substances e.g. are used as moisture retention regulators ("moisturizers"): sodium lactate, urea and derivatives, alcohols, glycerol, diols, such as propylene glycol, 1,2-pentanediol, 1,2-hexanediol and 1,2-octanediol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulfate, lanolin, lanolin esters, amino acids, alpha-hydroxy acids (e.g. citric acid, lactic acid, malic acid) and derivatives thereof, mono-, di- and oligosaccharides, such as, for example, glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts.

Formulations according to the invention can also be employed together with osmolytes. Osmolytes which may be mentioned by way of example are: substances from the group consisting of sugar alcohols (myo-inositol, mannitol, sorbitol), quaternary amines, such as taurine, choline, betaine, betaine-glycine and ectoin, diglycerol phosphate, phosphorylcholine, glycerophosphorylcholines, amino acids, such as glutamine, glycine, alanine, glutamate, aspartate or proline, phosphatidylcholine, phosphatidylinositol and inorganic phosphates, as well as polymers of the compounds mentioned, such as proteins, peptides, poly-amino acids and polyols. All osmolytes at the same time have a skin-moisturizing action.

Formulations according to the invention can advantageously also comprise vitamins and vitamin precursors, it being possible for all the vitamins and vitamin precursors which are suitable or usual for cosmetic and/or dermatological uses to be used. Vitamins and vitamin precursors which may be mentioned by way of example are: vitamin A (retinol) and its derivatives (e.g. vitamin A acetate, vitamin A acid, vitamin A aldehyde, vitamin A palmitate, vitamin A propionate), vitamin B1 (thiamine) and its salts (e.g. vitamin B1 hydrochloride, vitamin B1 mononitrate, thiamine diphosphate, thiamine pyrophosphate), vitamin B12 (cobalamin), vitamin B2 (vitamin G, riboflavin) and its derivatives (e.g. vitamin B2 tetraacetate), vitamin B3 and its derivatives (e.g. nicotinamide ascorbate, nicotinamide glycollate, nicotinamide hydroxycitrate, nicotinamide lactate, nicotinamide malate, nicotinamide mandelate, nicotinamide salicylate, nicotinamide thioctate), vitamin B4 (adenine) and its derivatives (e.g. adenine riboside, disodium flavin adenine dinucleotide, nicotinamide adenine dinucleotide), provitamin B5, vitamin B5 (pantothenic acid) and its derivatives (e.g. acetyl pantothenyl ethyl ether, allantoin calcium pantothenate, allantoin DL-pantothenyl alcohol, bis(pantothenamidoethyl) disulfide, calcium pantothenate, hydroxyethyl pantothenamide MEA, sodium pantothenate, N-D-pantothenoyl-2-(2-aminoethoxy)ethanol, N-D-pantothenoyl-2-aminoethanol, N-hydroxyethoxyethyl pantothenamide, N-hydroxyethyl pantothenamide, pantothenamide MEA, pantothenol, pantothenic acid lactone, pantothenic acid polypeptide, pantothenyl ethyl ether), vitamin B6 (pyridoxol, pyroxidal, pyridoxamine) and its derivatives (e.g. pyridoxine dicaprylate, vitamin B6 dilaurate, vitamin B6 dioctanoate, vitamin B6 dipalmitate, pyridoxine glycyrrhetinate, vitamin B6 hydrochloride, vitamin B6 phosphate, vitamin B6 serine, vitamin B6 tripalmitate), vitamin C (ascorbic acid) and its derivatives (e.g. 3-O-ethyl ascorbic acid, allantoin ascorbate, aminopropyl ascorbyl phosphate, araboascorbic acid, monosodium salt, ascorbic acid palmitate, ascorbic acid polypeptide, ascorbosilane C, ascorbyl dipalmitate, ascorbyl glucoside, ascorbyl inositol nicotinate, ascorbyl linoleate, ascorbyl methylsilanol pectinate, ascorbyl nicotinamide, ascorbyl phosphate magnesium, ascorbyl stearate, ascorbyl tetraisopalmitate, ascorbyl tocopheryl maleate, calcium ascorbate, chitosan ascorbate, D-arabino-ascorbic acid, disodium ascorbyl sulfate, glucosamine ascorbate, inositol hexanicotinate hexa-ascorbate, isoascorbic acid, L-ascorbic acid, 2-(dihydrogen phosphate), trisodium salt, L-ascorbic acid, 2-[(3-cholest-5-en-3-yl hydrogen phosphate], monosodium salt, L-ascorbic acid, 2-O-D-glucopyranosyl-, L-ascorbic acid, 3-O-ethyl ether, magnesium ascorbate, magnesium ascorbylborate, methoxy PEG-7 ascorbic acid, methylsilanol ascorbate, potassium ascorbyl tocopheryl phosphate, potassium ascorbylborate, sodium ascorbate, sodium ascorbyl phosphate, sodium ascorbyl/cholesteryl phosphate, sodium isoascorbate, sodium L-ascorbyl 2-phosphate, tetrahexyldecyl ascorbate), provitamin D, vitamin D (calciol) and its derivatives (e.g. vitamin D2, vitamin D3), vitamin E (D-alpha-tocopherol) and its derivatives (e.g. di-alpha-tocopherol, polyoxypropylene/polyoxyethylene/tocopherol ether, polypropylene glycol/tocopherol olypropylene glycol t, polyoxypropylene/polyoxyethylen tocopherol ether, polypropylene glycol trovitamin D, vitamin Dether, tocopherol cysteamine, tocopherol phosphate, sodium vitamin E phosphate, vitamin E acetate, vitamin E linoleate, vitamin E nicotinate, vitamin E succinate), vitamin F (essential fatty acids, linolenic acid and linoleic acid) and its derivatives (e.g. vitamin F ethyl ester, vitamin F glyceryl ester), vitamin H (vitamin B7, biotin), vitamin K1 (phylloquinone, phytonadione) and vitamin K3 (menadione, menaquinone).

Formulations according to the invention can likewise comprise one or more further plant extracts, which are conventionally prepared by extraction of the whole plant, but in individual cases also exclusively from blossom and/or leaves, wood, bark or roots of the plant. In respect of the plant extracts which can be used, reference is made in particular to the extracts which are listed in the table starting on page 44 of the 3rd edition of the Leitfaden zur Inhaltsstoffdeklaration kosmetischer Mittel [Manual of Declaration of the Constituents of Cosmetic Compositions], published by Industrieverband Körperpflegemittel und Waschmittel e.V. (IKW), Frankfurt. Extracts which are advantageous in particular are those from aloe, algae, apple, apricot, arnica, avocado, pear, stinging nettle, blackberry, calendula, ivy, hibiscus, oak bark, strawberry, spruce, honeysuckle, barley, ginkgo, ginseng, pomegranate, grapefruit, cucumber, oats, witch hazel, restharrow, henna, raspberry, elder, honeybush, hops, coltsfoot, kiwi, burdock, coconut, lavender, lime, linden, mallow, almond, mango, box holly, *Melissa*, olive, orange, peppermint, *Pueraria*, wild thyme, rooibos, rose, rosemary, horse chestnut, sage, sandalwood, yarrow, horsetail, *Sophora*, liquorice, dead nettle, tea (green, white, black), thyme, grape, juniper, willow, rose-bay willow-herb, hawthorn, wheat, lady's smock, cinnamon, lemon and lemongrass. In this context, the extracts from aloe vera, algae, arnica, stinging nettle, calendula, witch hazel, linden, ginseng, cucumber, rosemary and sage are particularly preferred. Mixtures of two or more plant extracts can also be employed. Extraction agents which can be used for the preparation of the plant extracts mentioned are, inter alia, water, alcohols and mixtures thereof. In this context, among the alcohols lower alcohols, such as ethanol and isopropanol, and also polyhydric alcohols, such as ethylene glycol, propylene glycol and butylene glycol, are preferred, and in particular both as the sole extraction agent and in mixtures with water. The plant extracts can be employed both in the pure and in the diluted form.

The formulations according to the invention (e.g. topical cosmetic formulation) advantageously comprise cooling agents. Cooling agents which may be mentioned by way of example are: l-menthol, d-menthol, racemic menthol, menthone glycerol acetal, menthyl lactate, substituted menthyl-3-carboxylic acid amides (e.g. menthyl-3-carboxylic acid N-ethylamide), 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxy-carboxylic acid esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and trioxaalkanoates, 3-menthyl methoxyacetate and icilin.

The formulations according to the invention moreover can also preferably comprise perspiration-inhibiting active compounds (antiperspirants) and odour absorbers. Perspiration-inhibiting active compounds which are employed are, above all, aluminium salts, such as aluminium chloride, aluminium hydrochloride, nitrate, sulfate, acetate etc. In addition, however, the use of compounds of zinc, magnesium and zirconium may also be advantageous. For use in cosmetic and dermatological antiperspirants, the aluminium salts and—to a somewhat lesser extent—aluminium/zirconium salt combinations have essentially proved suitable. The aluminium hydroxychlorides which are partly neutralized and therefore tolerated better by the skin, but not quite so active, are additionally worth mentioning. Alongside aluminium salts, further substances are also possible, such as, for example, a) protein-precipitating substances, such as, inter alia, formaldehyde, glutaraldehyde, natural and synthetic tannins and trichloroacetic acid, which bring about blockage of the sweat glands on the surface, b) local anaesthetics (inter alia dilute solutions of e.g. lidocaine, prilocalne or mixtures of such substances), which eliminate sympathetic supply of the sweat glands by blockade of the peripheral nerve pathways, c) zeolites of the X, A or Y type, which, alongside the reduction in secretion of perspiration, also function as adsorbents for bad odours, and d) botulinus toxin (toxin of the bacterium *Chlostridium botulinum*), which is also employed in cases of hyperhidrosis, a pathologically increased secretion of perspiration, and the action of which is based on an irreversible blocking of the release of the transmitter substance acetylcholine, which is relevant for secretion of perspiration.

Odour absorbers are, for example, the laminar silicates described in DE 40 09 347, and of these in particular montmorillonite, kaolinite, nontronite, saponite, hectorite, bentonite and smectite, and furthermore, for example, zinc salts of ricinoleic acid. These likewise include deodorants, bactericidal or bacteriostatic deodorizing substances, such as e.g. hexachlorophene, 2,4,4'-trichloro-2' hydroxydiphenyl ether (Irgasan), 1,6-di-(4-chlorophenylbiguanido)-hexane (chlorhexidine) and 3,4,4'-trichlorocarbanilide, as well as the active agents described in DE 37 40 186, DE 39 38 140, DE 42 04 321, DE 42 29 707, DE 42 29 737, DE 42 37 081, DE 43 09 372 and DE 43 24 219, and cationic substances, such as e.g. quaternary ammonium salts, and odour absorbers, such as e.g. ®Grillocin (combination of zinc ricinoleate and various additives) or triethyl citrate, optionally in combination with ion exchange resins.

In various cases it may also be advantageous to employ formulations according to the invention in combination with substances which are chiefly employed for inhibition of the growth of undesirable microorganisms on or in animal organisms. In this respect, alongside conventional preservatives, further active compounds which are worth mentioning, alongside the large group of conventional antibiotics, are, in particular, the products relevant for cosmetics, such as triclosan, climbazole, zinc pyrithione, ichthyol, Octopirox (1-hydroxy-4-methyl-6-(2,4,4-trimethylpentyl)-2(1H)-pyridone, 2-aminoethanol), chitosan, farnesol, octoxyglycerol, glycerol monolaurate, arylalkyl alcohols, such as e.g. phenylethyl alcohol, 3-phenyl-1-propanol, veticol or muguet alcohol, polyglycerol esters, such as e.g. polyglyceryl 3-caprylates, and aliphatic diols, such as e.g. 1,2-decanediol, or combinations of the substances mentioned, which are employed, inter alia, against underarm odour, foot odour or dandruff formation.

Formulations according to the invention can in numerous cases also advantageously comprise preservatives. Preservatives which are preferably chosen here are those such as benzoic acid and its esters and salts, propionic acid and its esters and salts, salicylic acid and its esters and salts, 2,4-hexadienoic acid (sorbic acid) and its esters and salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)$_5$-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-di methyl phenol, 1,1'-methylene-bis(3-(1-hydroxymethyl-2,4-dioximidazolidin-5-yl)urea), poly-(hexamethylene-diguanide) hydrochloride, 2-phenoxyethanol, hexamethylenetetramine, 1-(3-chloroallyl)-3,5,7-triaza-1-azoniaadamantane chloride, 1-(4-chlorophenoxy)-1-(1H-imidazol-1-yl)-3,3-dimethyl-2-butanone, 1,3-bis-(hydroxy-methyl)-5, 5-dimethyl-2,4-imidazolidinedione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3 (2H)-isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$)trimethyl-ammonium bromide and chloride, 4,4-di methyl-1,3-oxazolidine, N-hydroxymethyl-N-(1, 3-di(hydroxymethyl)-2,5-dioxoimidazolidin-4-yl)-N'-hydroxy-methylurea, 1,6-bis(4-amidino-phenoxy)-n-hexane and its salts, glutaraldehyde, 5-ethyl-1-aza-3,7-dioxabicyclo (3.3.0)octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate or sodium hydroxymethyl-aminoacetate.

Formulations according to the invention can also comprise anionic, cationic, nonionic and/or amphoteric surfactants, especially if crystalline or microcrystalline solids, for example inorganic micropigments, are to be incorporated into the formulations. Surfactants are amphiphilic substances which can dissolve organic, nonpolar substances in water. In this context, the hydrophilic contents of a surfactant molecule are usually polar functional groups, for example —COO$^-$, —OSO$_3^{2-}$ or —SO$_3^-$, while the hydrophobic parts as a rule are nonpolar hydrocarbon radicals. Surfactants are in general classified according to the nature and charge of the hydrophilic molecular moiety. A distinction can be made between four groups here:

anionic surfactants,
cationic surfactants,
amphoteric surfactants and
nonionic surfactants.

Anionic surfactants as a rule contain carboxylate, sulfate or sulfonate groups as functional groups. In aqueous solution, they form negatively charged organic ions in an acid or neutral medium. Cationic surfactants are almost exclusively characterized by the presence of a quaternary ammonium group. In aqueous solution, they form positively charged organic ions in an acid or neutral medium. Amphoteric surfactants contain both anionic and cationic groups and accordingly behave like anionic or cationic surfactants in aqueous solution, depending on the pH. In a strongly acid medium they have a positive charge, and in an alkaline medium a negative charge. On the other hand, they are zwitter-ionic in the neutral pH range. Polyether chains are typical of nonionic surfactants. Nonionic surfactants do not form ions in an aqueous medium.

A. Anionic Surfactants

Anionic surfactants which are advantageously to be used are acylamino acids (and salts thereof), such as
  acyl glutamates, for example sodium acyl glutamate, di-TEA-palmitoyl aspartate and sodium caprylic/capric glutamate,
  acyl peptides, for example palmitoyl hydrolysed milk protein, sodium cocoyl hydrolysed soya protein and sodium/potassium cocoyl hydrolysed collagen,
  sarcosinates, for example myristoyl sarcosine, TEA-lauroyl sarcosinate, sodium lauroyl sarcosinate and sodium cocoyl sarcosinate,
  taurates, for example sodium lauroyl taurate and sodium methylcocoyl taurate,
  acyl lactylates, lauroyl lactylate and caproyl lactylate alaninates
carboxylic acids and derivatives, such as
for example, lauric acid, aluminium stearate, magnesium alkanolate and zinc undecylenate,
  ester-carboxylic acids, for example calcium stearoyl lactylate, laureth-6 citrate and sodium PEG-4 lauramide carboxylate,
  ether-carboxylic acids, for example sodium laureth-13 carboxylate and sodium PEG-6 cocamide carboxylate,
phosphoric acid esters and salts, such as, for example, DEA-oleth-10 phosphate and dilaureth-4 phosphate,
sulfonic acids and salts, such as
  acyl isethionates, e.g. sodium/ammonium cocoyl isethionate,
  alkylarylsulfonates,
  alkylsulfonates, for example sodium coconut monoglyceride sulfate, sodium $C_{12-14}$ olefin-sulfonate, sodium lauryl sulfoacetate and magnesium PEG-3 cocamide sulfate,
  sulfosuccinates, for example dioctyl sodium sulfosuccinate, disodium laureth-sulfosuccinate, disodium laurylsulfosuccinate and disodium undecylenamido-MEA-sulfosuccinate
and
sulfuric acid esters, such as
  alkyl ether-sulfate, for example sodium, ammonium, magnesium, MIPA and TIPA laureth sulfate, sodium myreth sulfate and sodium C12-13 pareth sulfate,
  alkyl sulfates, for example sodium, ammonium and TEA lauryl sulfate.

B. Cationic Surfactants

Cationic surfactants which are advantageously to be used are
  alkylamines,
  alkylimidazoles,
  ethoxylated amines and
  quaternary surfactants,
    $RNH_2CH_2CH_2COO^-$ (at pH=7)
    $RNHCH_2CH_2COO-B^+$ (at pH=12) $B^+$=any desired cation, e.g. $Na^+$
  ester quats Quaternary surfactants contain at least one N atom which is covalently bonded to 4 alkyl or aryl groups. This leads to a positive charge, independently of the pH. Alkylbetaine, alkylamidopropylbetaine and alkylamidopropylhydroxysulfaine are advantageous. The cationic surfactants used can furthermore preferably be chosen from the group consisting of quaternary ammonium compounds, in particular benzyltrialkylammonium chlorides or bromides, such as, for example, benzyldimethylstearyl-ammonium chloride, furthermore alkyltrialkylammonium salts, for example cetyltrimethylammonium chloride or bromide, alkyldimethylhydroxy-ethylammonium chlorides or bromides, dialkyldimethylammonium chlorides or bromides, alkylamidoethyltrimethylammonium ether-sulfates, alkylpyridinium salts, for example lauryl- or cetylpyrimidinium chloride, imidazoline derivatives and compounds having a cationic character, such as amine oxides, for example alkyldimethylamine oxides or alkylaminoethyldimethylamine oxides. Cetyltrimethyl-ammonium salts in particular are advantageously to be used.

C. Amphoteric Surfactants

Amphoteric surfactants which are advantageously to be used are
  acyl-/dialkylethylenediamine, for example sodium acylamphoacetate, disodium acylamphodipropionate, disodium alkylamphodiacetate, sodium acylamphohydroxypropylsulfonate, disodium acylamphodiacetate and sodium acylamphopropionate,
  N-alkylamino acids, for example aminopropyl alkylglutamide, alkylaminopropionic acid, sodium alkylimidodipropionate and lauroamphocarboxyglycinate.

D. Nonionic Surfactants

Nonionic surfactants which are advantageously to be used are
  alcohols,
  alkanolamides, such as cocamides MEA/DEA/MIPA,
  amine oxides, such as cocoamidopropylamine oxide,
  esters which are formed by esterification of carboxylic acids with ethylene oxide, glycerol, sorbitan or other alcohols,
  ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and coconut glycoside.
  sucrose esters and ethers
  polyglycerol esters, diglycerol esters, monoglycerol esters
  methylglucose esters, esters of hydroxy acids The use of a combination of anionic and/or amphoteric surfactants with one or more nonionic surfactants is furthermore advantageous.

The surface-active substance can be present in a concentration of between 1 and 98 wt. % in the formulations according to the invention, based on the total weight of the formulations.

Cosmetic or dermatological formulations which comprise formulations according to the invention can also be in the form of emulsions.

The oily phase can advantageously be chosen from the following substance group:
  mineral oils, mineral waxes
  fatty oils, fats, waxes and other natural and synthetic fat substances, preferably esters of fatty acids with alcohols of low C number, e.g. with isopropanol, propylene glycol or glycerol, or esters of fatty alcohols with alkanoic acids of low C number or with fatty acids;
  alkyl benzoates;
  silicone oils, such as dimethylpolysiloxanes, diethylpolysiloxanes, diphenylpolysiloxanes and mixed forms thereof.

Compounds which can advantageously be employed are (a) esters of saturated and/or unsaturated branched and/or unbranched alkanecarboxylic acids having a chain length of from 3 to 30 C atoms and saturated and/or unsaturated, branched and/or unbranched alcohols having a chain length of from 3 to 30 C atoms, (b) esters of aromatic carboxylic acids and saturated and/or unsaturated, branched and/or unbranched alcohols having a chain length of from 3 to 30 C atoms. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

The oily phase can furthermore advantageously be chosen from the group consisting of branched and unbranched hydrocarbons and waxes, silicone oils and dialkyl ethers, the group consisting of saturated or unsaturated, branched or unbranched alcohols, and the fatty acid triglycerides, namely the triglycerol esters of saturated and/or unsaturated, branched and/or unbranched alkanecarboxylic acids having a chain length of from 8 to 24, in particular 12 to 18 C atoms. The fatty acid triglycerides can advantageously be chosen from the group consisting of synthetic, semi-synthetic and natural oils, e.g. olive oil, sunflower oil, soya oil, groundnut oil, rapeseed oil, almond oil, palm oil, coconut oil, palm kernel oil and more of the like. Any desired blends of such oil and wax components can also advantageously be employed. In some cases it is also advantageous to employ waxes, for example cetyl palmitate, as the sole lipid component of the oily phase, and the oily phase is advantageously chosen from the group which consists of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oily phase can furthermore have a content of cyclic or linear silicone oils or consist entirely of such oils, it nevertheless being preferable to use an additional content of other oily phase components in addition to the silicone oil or silicone oils. Cyclomethicone (e.g. decamethylcyclopentasiloxane) can advantageously be employed as a silicone oil. However, other silicone oils, for example undecamethylcyclotrisiloxane, polydimethylsiloxane and poly(methyl-phenylsiloxane), can also advantageously be used. Mixtures of cyclomethicone and isotridecyl isononanoate and of cyclomethicone and 2-ethylhexyl isostearate are furthermore particularly advantageous.

The aqueous phase of formulations according to the invention which are in the form of an emulsion can advantageously comprise: alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, e.g. ethanol, isopropanol, 1,2-propanediol and glycerol, and, in particular, one or more thickening agents, which can advantageously be chosen from the group consisting of silicon dioxide, aluminium silicates, polysaccharides and derivatives thereof, e.g. hyaluronic acid, xanthan gum and hydroxypropyl-methylcellulose, particularly advantageously from the group consisting of polyacrylates, preferably a polyacrylate from the group consisting of the so-called Carbopols, for example Carbopols of the types 980, 981, 1382, 2984 and 5984, in each case individually or in combination.

Formulations in the form of an emulsion which comprise a formulation according to the invention advantageously comprise one or more emulsifiers. O/W emulsifiers can advantageously be chosen, for example, from the group consisting of polyethoxylated or polypropoxylated or polyethoxylated and polypropoxylated products, e.g.:
  the fatty alcohol ethoxylates
  the ethoxylated wool wax alcohols,
  the polyethylene glycol ethers of the general formula R—O—(—CH$_2$—CH$_2$—O—)$_n$—R',
  the fatty acid ethoxylates of the general formula R—COO—(—CH$_2$—CH$_2$—O—)$_n$—H,
  the etherified fatty acid ethoxylates of the general formula R—COO—(—CH$_2$—CH$_2$—O—)$_n$—R', the esterified fatty acid ethoxylates of the general formula R—COO—(—CH$_2$—CH$_2$—O—)$_n$—C(O)—R', the polyethylene glycol glycerol fatty acid esters
  the ethoxylated sorbitan esters
  the cholesterol ethoxylates
  the ethoxylated triglycerides
  the alkyl ether-carboxylic acids of the general formula R—COO—(—CH$_2$—CH$_2$—O—)$_n$—OOH, wherein n represents a number from 5 to 30, the polyoxyethylene sorbitol fatty acid esters,
  the alkyl ether-sulfates of the general formula R—O—(—CH$_2$—CH$_2$—O—)$_n$—SO$_3$—H
  the fatty alcohol propoxylates of the general formula R—O—(—CH$_2$—CH(CH$_3$)—O—)$_n$—H
  the polypropylene glycol ethers of the general formula R—O—(—CH$_2$—CH(CH$_3$)—O—)$_n$—R' the propoxylated wool wax alcohols,
  the etherified fatty acid propoxylates R—COO—(—CH$_2$—CH(CH$_3$)—O—)$_n$—R'
  the esterified fatty acid propoxylates of the general formula R—COO—(—CH$_2$—CH(CH$_3$)—O—)$_n$—C(O)—R' the fatty acid propoxylates of the general formula

R—COO—(—CH$_2$—CH(CH$_3$)—O—)$_n$—H, the polypropylene glycol glycerol fatty acid esters
the propoxylated sorbitan esters
the cholesterol propoxylates
the propoxylated triglycerides
the alkyl ether-carboxylic acids of the general formula

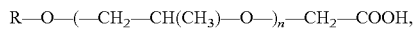
R—O—(—CH$_2$—CH(CH$_3$)—O—)$_n$—CH$_2$—COOH, the alkyl ether-sulfates and the acids on which these sulfates are based
of the general formula R—O—(—CH$_2$—CH(CH$_3$)—O—)$_n$—SO$_3$—H,
the fatty alcohol ethoxylates/propoxylates of the general formula R—O—X$_n$—Y$_m$—H
the polypropylene glycol ethers of the general formula R—O—X$_n$—Y$_m$—R'
the etherified fatty acid propoxylates of the general formula R—COO—X$_n$—Y$_m$—R'
the fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers employed are particularly advantageously chosen from the group consisting of substances having HLB values of 11-18, very particularly advantageously having HLB values of 14.5-15.5, if the O/W emulsifiers contain saturated radicals R and R'. If the O/W emulsifiers contain unsaturated radicals R and/or R', or isoalkyl derivatives are present, the preferred HLB value of such emulsifiers can also be lower or higher.

It is of advantage to choose the fatty alcohol ethoxylates from the group consisting of ethoxylated stearyl alcohols, cetyl alcohols and cetyl stearyl alcohols (cetearyl alcohols). The following are particularly preferred:
polyethylene glycol(13) stearyl ether (steareth-13), polyethylene glycol(14) stearyl ether (steareth-14), polyethylene glycol(15) stearyl ether (steareth-15), polyethylene glycol(16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20), polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20), polyethylene glycol(13) cetyl ether (ceteth-13), polyethylene glycol(14) cetyl ether (ceteth-14), polyethylene glycol(15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20), polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20), polyethylene glycol(12) oleyl ether (oleth-12), polyethylene glycol(13) oleyl ether (oleth-13), polyethylene glycol(14) oleyl ether (oleth-14), polyethylene glycol(15) oleyl ether (oleth-15), polyethylene glycol(12) lauryl ether (laureth-12), polyethylene glycol(12) isolauryl ether (isolaureth-12), polyethylene glycol(13) cetyl stearyl ether (ceteareth-13), polyethylene glycol(14) cetyl stearyl ether (ceteareth-14), polyethylene glycol(15) cetyl stearyl ether (ceteareth-15), polyethylene glycol(16) cetyl stearyl ether (ceteareth-16), polyethylene glycol(17) cetyl stearyl ether (ceteareth-17), polyethylene glycol(18) cetyl stearyl ether (ceteareth-18), polyethylene glycol(19) cetyl stearyl ether (ceteareth-19) and polyethylene glycol(20) cetyl stearyl ether (ceteareth-20).

It is furthermore advantageous to chose the fatty acid ethoxylates from the following group:
polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate.

Sodium laureth-11 carboxylate can advantageously be used as an ethoxylated alkyl ether-carboxylic acid or salt thereof. Sodium laureth 1-4 sulfate can advantageously be used as an alkyl ether-sulfate. Polyethylene glycol(30) cholesteryl ether can advantageously be used as an ethoxylated cholesterol derivative. Polyethylene glycol(25) sojasterol has also proved suitable.

The polyethylene glycol(60) evening primrose glycerides can advantageously be used as ethoxylated triglycerides.

It is furthermore advantageous to choose the polyethylene glycol glycerol fatty acid esters from the group consisting of polyethylene glycol(20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate/caproate, polyethylene glycol(20) glyceryl oleate, polyethylene glycol(20) glyceryl isostearate and polyethylene glycol(18) glyceryl oleate/cocoate.

It is likewise favourable to choose the sorbitan esters from the group consisting of polyethylene glycol(20) sorbitan monolaurate, polyethylene glycol(20) sorbitan monostearate, polyethylene glycol(20) sorbitan monoisostearate, polyethylene glycol(20) sorbitan monopalmitate and polyethylene glycol(20) sorbitan monooleate.

Advantageous W/O emulsifiers which can be employed are: fatty alcohols having 8 to 30 carbon atoms, monoglycerol esters of saturated and/or unsaturated, branched and/or unbranched alkanecarboxylic acids having a chain length of from 8 to 24, in particular 12 to 18 C atoms, diglycerol esters of saturated and/or unsaturated, branched and/or unbranched alkanecarboxylic acids having a chain length of from 8 to 24, in particular 12 to 18 C atoms, monoglycerol ethers of saturated and/or unsaturated, branched and/or unbranched alcohols having a chain length of from 8 to 24, in particular 12 to 18 C atoms, diglycerol ethers of saturated and/or unsaturated, branched and/or unbranched alcohols having a chain length of from 8 to 24, in particular 12 to 18 C atoms, propylene glycol esters of saturated and/or unsaturated, branched and/or unbranched alkanecarboxylic acids having a chain length of from 8 to 24, in particular 12 to 18 C atoms and sorbitan esters of saturated and/or unsaturated, branched and/or unbranched alkanecarboxylic acids having a chain length of from 8 to 24, in particular 12 to 18 C atoms.

W/O emulsifiers which are advantageous in particular are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaproate and glyceryl monocaprylate.

Formulations according to the invention for topical prophylactic or cosmetic treatment of the skin can regularly comprise a high content of care substances. According to a preferred embodiment, the compositions comprise one or more animal and/or plant fats and oils having care properties, such as olive oil, sunflower oil, refined soya oil, palm oil, sesame oil, rapeseed oil, almond oil, borage oil, evening primrose oil, coconut oil, shea butter, jojoba oil, oat oil, sperm oil, beef tallow, neat's foot oil and lard, and optionally further care constituents, such as, for example, fatty alcohols having 8-30 C atoms. The fatty alcohols here can be saturated or unsaturated and linear or branched. Alcohols which can be employed are, for example, decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol, and Guerbet alcohols thereof, it being possible for the list to be extended virtually as desired by further alcohols of related structural chemistry. The fatty alcohols preferably originate from natural fatty acids, being conventionally prepared from the corresponding esters of the fatty acids by reduction. Fatty alcohol fractions which are formed by reduction from naturally occurring fats and fatty oils, such as e.g. beef tallow, groundnut oil, colza oil, cottonseed oil, soya oil, sunflower oil, palm kernel oil, linseed oil, maize oil, castor oil, rape oil, sesame oil, cacao butter and coconut fat, can furthermore be employed.

Care substances which can be combined in an outstanding manner with formulations according to the invention moreover also include waxes, such as e.g. candelilla wax or carnauba wax ceramides, where ceramides are understood as meaning N-acylsphingosins (fatty acid amides of sphingosin) or synthetic analogues of such lipids (so-called pseudoceramides), which significantly improve the water retention capacity of the stratum corneum.

phospholipids, for example soya lecithin, egg lecithin and cephalins vaseline, paraffin oils and silicone oils; the latter include, inter alia, dialkyl- and alkylarylsiloxanes, such as dimethylpolysiloxane and methylphenylpolysiloxane, as well as alkoxylated and quaternized derivatives thereof.

The invention also provides the use of a formulation according to the invention or of a medicament according to the invention for prophylaxis of skin irritations and/or for treatment of skin irritations for medical and/or other than medical purposes. The invention likewise provides the use of a formulation according to the invention or of a medicament according to the invention for the preparation of a medicament for treatment of skin irritations.

The invention furthermore provides the use of a formulation according to the invention or of a medicament according to the invention for the preparation of a cosmetic or pharmaceutical formulation.

The invention also provides the use of a formulation according to the invention or of a medicament according to the invention for reducing, eliminating or suppressing the skin-irritating action of a substance or substance mixture.

The advantage of the uses according to the invention lies in particular in that due to the synergistic effect of the components contained in the formulation according to the invention or in the medicament according to the invention in respect of the skin irritation-reducing action, relatively low active combinations are sufficient. This reduces the probability of a renewed allergic reaction, and can include cost advantages and contribute towards protecting the environment.

The invention also provides a process for the preparation of a formulation according to the invention or of a medicament according to the invention, with the following steps:

provision of bisabolol, provision of a composition or compound chosen from the group consisting of a) substance mixtures obtainable from an extraction of ginger, b) substance mixtures obtainable from a separation of a ginger extract which comprise a compound which is chosen from the group consisting of gingerols, shogaols, gingerdiols, dehydrogingerdiones, paradols and derivatives thereof and c) compounds obtainable from a separation of a ginger extract which are chosen from the group consisting of gingerols, shogaols, gingerdiols, dehydrogingerdiones, paradols and derivatives thereof mixing of the components provided, so that the particular content of bisabolol and that of the said composition or compound in the mixture is adjusted such that the skin irritation-reducing action of these contents is increased synergistically.

The invention likewise provides a cosmetic or therapeutic method for prophylaxis of skin irritation, with the following steps:

provision of a formulation according to the invention or of a medicament according to the invention and application of the formulation or of the medicament to non-irritated skin in an active amount.

The invention furthermore provides a cosmetic or therapeutic method for treatment of skin irritation, with the following steps:

provision of a formulation according to the invention or of a medicament according to the invention and application of the formulation or of the medicament to irritated skin in an active amount.

The invention furthermore provides a method for prophylaxis of the skin-irritating action or for reducing, eliminating or suppressing the skin-irritating action of a substance or substance mixture, with the following steps:

provision of a substance or substance mixture having a skin-irritating action, provision of bisabolol, provision of a composition or compound chosen from the group consisting of a) substance mixtures obtainable from an extraction of ginger, b) substance mixtures obtainable from a separation of a ginger extract which comprise a compound which is chosen from the group consisting of gingerols, shogaols, gingerdiols, dehydrogingerdiones, paradols and derivatives thereof and c) compounds obtainable from a separation of a ginger extract which are chosen from the group consisting of gingerols, shogaols, gingerdiols, dehydrogingerdiones, paradols and derivatives thereof
bringing together of the last two components provided with the substance or substance mixture having a skin-irritating action, so that the skin-irritating action is reduced, eliminated or suppressed and a formulation according to the invention or a medicament according to the invention is formed.

One advantage of the method according to the invention mentioned last is that the skin-irritating action of compounds or compound mixtures can be moderated in this way to the extent that they are accessible for uses for which they were hitherto not available. On the basis of the method according to the invention mentioned last, higher concentrations of skin-irritating compounds and mixtures can also be employed in uses where there is the possibility of skin contact. In this context, it is particularly preferable if, on the basis of the method according to the invention mentioned last, the skin-irritating action of the skin-irritating compound is eliminated completely (i.e. it no longer exists) or is suppressed completely (i.e. it no longer has an effect). The method according to the invention mentioned last can be employed, for example, against the skin-irritating action of detergents and allergy-inducing substances.

For the methods and uses mentioned, the ratios of amounts or contents of components (A) and (B) and of the formulation according to the invention which are described above as preferred likewise apply.

The invention also provides a kit which comprises a formulation according to the invention or of a medicament according to the invention. Using such a kit, for example, after series of tests to test skin-irritating substances, the areas of skin tested can be treated for regeneration.

Preferred embodiments and further aspects of the present invention emerge from the attached patent claims and the following examples, the examples not being intended to limit the invention.

EXAMPLES 1-10

Formulations Comprising a Formulation According to the Invention Having a Skin Irritation-Reducing Action In the following table 1
1=Skin-lightening day cream O/W
2=Skin-soothing lotion with plant extracts O/W
3=Aftersun balm
4=Body spray
5=Sunscreen lotion (O/W), broad-band protection
6=W/O night cream
7=Shampoo
8=Self-tanning cream
9=Barrier repair cream O/W
10=Antiperspirant/deodorant roll-on

TABLE 1

| RAW MATERIAL NAME (MANUFACTURER) | INCI | % BY WEIGHT | | | | | | | | | |
|---|---|---|---|---|---|---|---|---|---|---|---|
| | | 1 | 2 | 3 | 4 | 5 | 6 | 7 | 8 | 9 | 10 |
| -(-Alpha-)-Bisabolol, natural (Symrise) | Bisabolol | 0.3 | 0.4 | 0.3 | 0.1 | 0.3 | 0.2 | 0.05 | 0.2 | 0.5 | 0.1 |
| Ginger $CO_2$ Extract (Flavex) | *Zingiber Officinale* (Ginger) Root Extract | 0.003 | 0.004 | 0.003 | 0.005 | 0.003 | 0.002 | 0.001 | 0.002 | 0.01 | 0.001 |
| Abil 350 (Degussa-Goldschmidt) | Dimethicone | 0.5 | 2.0 | 1.0 | | | | | 0.5 | 0.5 | |
| Allantoin (Merck) | Allantoin | | 0.2 | 0.1 | | | | | | | |
| Aloe Vera Gel Concentrate 10/1 (Symrise) | Water (Aqua), *Aloe Barbadensis* Leaf Juice | | | 3.0 | | | 3.0 | | | | |
| Alugel 34 TH (Baerlocher) | Aluminium Stearate | | | | | | | | 1.0 | | |
| Aqua-Ceramide (Kao) | Cetyloxypropyl Glyceryl Methoxypropyl Myristamide | | 0.1 | | | | | | | | 0.1 |
| Arbutin (Sabinsa) | β-Arbutin | 1.0 | | | | | | | | | |
| Sodium Ascorbyl Phosphate (EMD Chemicals) | Sodium Ascorbyl Phosphate | 2.0 | | 1.0 | | | | | | | |
| Butylene Glycol | Butylene Glycol | | | 5.0 | | | | | | | |
| Carbopol ETD 2050 (Noveon) | Carbomer | | | | | | 0.2 | | | | |
| Carbopol Ultrez-10 (Noveon) | Carbomer | | 0.1 | | | | | | | | |
| Ceramide 2 (Sederma) | Ceramide 2 | 0.1 | | | | | | | | | |
| Ceramide PC104 (Pacific | Hydroxypropyl Bispalmitamide | | | | | | | | | 0.1 | |

TABLE 1-continued

| RAW MATERIAL NAME (MANUFACTURER) | INCI | % BY WEIGHT | | | | | | | | | |
|---|---|---|---|---|---|---|---|---|---|---|---|
| | | 1 | 2 | 3 | 4 | 5 | 6 | 7 | 8 | 9 | 10 |
| Corporation) | MEA | | | | | | | | | | |
| Ceramide SL (Sino Lion) | Hydroxyethyl Palmityl Oxyhydroxypropyl Palmitamide | | | | | | 0.1 | | | | |
| Cetiol OE (Cognis) | Dicaprylyl Ether | | | 4.0 | | | | | | | |
| Cetiol SB 45 (Cognis) | *Butyrospermum Parkii* (Shea Butter) | | | 1.0 | | | | | | | |
| Citric Acid 10% sol. | Citric Acid | | | | | | | | 0.3 | | |
| Comperlan 100 (Cognis) | Cocamide MEA | | | | | | | | 0.5 | | |
| Dihydroxy-acetone (Merck) | Dihydroxyacetone | | | | | | | | | 5.0 | |
| Dow Corning 246 Fluid (Dow Corning) | Cyclohexasiloxane and Cyclopentasiloxane | | | | | | 2.0 | | | | |
| Dow Corning 345 Fluid (Dow Corning) | Cyclomethicone | | | | | 0.5 | | | | | |
| D-Panthenol (BASF) | Panthenol | | | | 1.0 | | | | | | |
| Dracorin CE (Symrise) | Glyceryl Stearate Citrate | 5.0 | | | | | | | 5.0 | 1.5 | |
| Dracorin GMS (Symrise) | Glyceryl Stearate | | 2.0 | | | | | | | 2.0 | |
| Dracorin GOC (Symrise) | Glyceryl Oleate Citrate, Caprylic/Capric Triglyceride | | | | 2.0 | | | | | | |
| Drago-Beta-Glucan (Symrise) | Water (Aqua), Butylene Glycol, Glycerin, *Avena Sativa* (Oat), Kernel Extract | 0.3 | | | | | | | | | |
| Dragocid Liquid (Symrise) | Phenoxyethanol, Methylparaben, Ethylparaben, Butylparaben, Propylparaben, Isobutylparaben | | 0.8 | 0.7 | | 0.7 | 0.8 | | | 0.8 | |
| Dragoderm (Symrise) | Glycerin, *Triticum Vulgare* (Wheat) Gluten, Water (Aqua) | | | | | | | | 2.0 | | |
| Drago-Oat-Active (Symrise) | Water (Aqua), Butylene Glycol, *Avena Sativa* (Oat) Kernel Extract | | | | | 1.0 | | | | | |
| Dragosan W/O Liquid (Symrise) | Polyglyceryl-3-Polyricinoleate, Sorbitan Isostearate | | | | | | 1.0 | | | | |
| Dragosan W/O P (Symrise) | Sorbitan Isostearate, Hydrogenated Castor Oil, Ceresin, Beeswax (Cera Alba) | | | | | | 6.0 | | | | |
| Dragoxat EH (Symrise) | Ethylhexyl Ethylhexanoate | 3.0 | 3.0 | | 4.0 | | | | 3.0 | | |
| Dragoxat 89 (Symrise) | Ethylhexyl Ethylisononanoate | | | | | | | | | 2.0 | |
| EDETA B Powder (BASF) | Tetrasodium EDTA | | | | | | | | 0.1 | | |
| EDETA DB (BASF) | Disodium EDTA | | | | | 0.1 | | | 0.1 | | |

TABLE 1-continued

| RAW MATERIAL NAME (MANUFACTURER) | INCI | % BY WEIGHT | | | | | | | | | |
|---|---|---|---|---|---|---|---|---|---|---|---|
| | | 1 | 2 | 3 | 4 | 5 | 6 | 7 | 8 | 9 | 10 |
| Emulsiphos (Symrise) | Potassium Cetyl Phosphate, Hydrogenated Palm Glycerides | | 2.0 | | | 1.5 | | | | 2.0 | |
| Ethanol 96% | Ethanol | | | | | | | | 2.0 | | 30.0 |
| Extrapone Green Tea GW (Symrise) | Glycerin, Water (Aqua), *Camellia Sinensis* Leaf Extract | | 0.2 | | | | | | | | |
| Extrapone Witch Hazel Distillate colourless (Symrise) | Propylene Glycol, *Hamamelis Virginiana* (Witch Hazel) Water, Water (Aqua), *Hamamelis Virginiana* (Witch Hazel) Extract | | | | | | 1.0 | | | | |
| Extrapone Rosemary GW (Symrise) | Glycerin, Water (Aqua), *Rosmarinus officinalis* (Rosemary) Leaf Extract | | 0.3 | | | | | | | 0.5 | |
| Farnesol (Symrise) | Farnesol | | | | | | | | | | 0.5 |
| Frescolat ML cryst. (Symrise) | Menthyl Lactate | | | | 0.8 | | | | | | |
| Genapol LRO liquid (Cognis) | Sodium Laureth Sulfate | | | | | | | 37.0 | | | |
| Givobio GZN (Seppic) | Zinc Gluconate | | | | | | | | | 0.5 | |
| Glycerol 85% | Glycerin | 3.0 | 2.0 | 4.0 | | 4.7 | 2.0 | | 1.5 | 3.0 | |
| Hydrolite-5 (Symrise) | Pentylene Glycol | | | | 5.0 | | | | 3.5 | | |
| Hydroviton (Symrise) | Water, Glycerin, Sodium Lactate, TEA Lactate, Serine, Lactic Acid, Urea, Sorbitol, Sodium Chloride, Lauryl Diethylenediaminoglycine, Lauryl Aminopropylglycine, Allantoin | | | | | | | | | 1.0 | |
| Irgasan DP 300 (Ciba Geigy) | Triclosan | | | | | | | | | | 0.3 |
| Isodragol (Symrise) | Triisononanoin | | 2.0 | | | | | | | 3.0 | |
| Isopropyl palmitate (Symrise) | Isopropyl Palmitate | 4.0 | | | | | | | 4.0 | | |
| Karion F (Merck) | Sorbitol | | | | | | 2.0 | | | | |
| Keltrol RD (CP-Kelco) | Xanthan Gum | 0.2 | 0.1 | | | | | | | | |
| Keltrol T (Danby-Chemie) | Xanthan Gum | | | | | 0.2 | | | 0.3 | | |
| Kojic acid (Cosmetochem) | Kojic Acid | 1.0 | | | | | | | | | |
| Lanette 16 (Cognis) | Cetyl Alcohol | 1.0 | | | | | | | 1.0 | | |
| Lanette O (Cognis) | Cetearyl Alcohol | | 3.0 | | | 1.0 | | | | 2.0 | |
| Lara Care A-200 (Rahn) | Galactoarabinan | | | 0.3 | | | | | | | |
| Magnesium Chloride (Merck) | Magnesium Chloride | | | | | | 0.7 | | | | |
| Merquat 550 (Ondeo Nalco) | Polyquaternium-7 | | | | | | | | 0.5 | | |
| NaOH 10% sol. | Sodium Hydroxide | | | | | | | | | 0.3 | |

TABLE 1-continued

| RAW MATERIAL NAME (MANUFACTURER) | INCI | % BY WEIGHT | | | | | | | | | |
|---|---|---|---|---|---|---|---|---|---|---|---|
| | | 1 | 2 | 3 | 4 | 5 | 6 | 7 | 8 | 9 | 10 |
| Naringin (Exquim) | 4',5,7-Trihydroxyflavone 7-O-Neohesperidoside | | | | | | | 0.5 | 2.0 | | |
| Sodium benzoate | Sodium Benzoate | | | | | | | 0.5 | | | |
| Natrosol 250 HHR (Aqualon) | Hydroxyethyl-cellulose | | | | | | | | | | 0.3 |
| Neo Heliopan 357 (Symrise) | Butyl Methoxy-dibenzoyl-methane | | | | | 1.0 | | | | | |
| Neo Heliopan AP (Symrise) (10% as sodium salt) | Disodium Phenyl Dibenzimidazole Tetrasulfonate | | | | | 10 | | | | | |
| Neo Heliopan AV (Symrise) | Ethylhexyl Methoxy-cinnamate | | | | | 3.0 | | | | | |
| Neo Heliopan Hydro (Symrise) (15% as sodium salt) | Phenylbenz-imidazole Sulfonic Acid | | | | | 6.7 | | | | | |
| Neo Heliopan MBC (Symrise) | 4-Methylbenzyl-idene Camphor | | | | | 1.5 | | | | | |
| Neo Heliopan OS (Symrise) | Ethylhexyl Salicylate | | | | | 5.0 | | | | | |
| Neutral Oil | Caprylic/Capric Triglyceride | 6.0 | | | 4.0 | 2.0 | | | 6.0 | 10.0 | |
| Oxynex 2004 (Merck) | BHT | | | | | | | 0.1 | | | |
| Paraffin oil 5 Grade E (Parafluid) | Paraffinum Liquidum | | | | 4.0 | | | | | | |
| PCL Liquid 100 (Symrise) | Cetearyl Ethylhexoate | 3.0 | 5.0 | | 7.0 | | | | | | |
| PCL Solid (Symrise) | Stearyl Heptanoate, Stearyl Caprylate | | 2.0 | | | | | | | | |
| PCL-Liquid (Symrise) | Cetearyl Ethylhexanoate, Isopropyl Myristate | | | | | | | 12.0 | 3.0 | | |
| Pemulen TR-2 (Noveon) | Acrylates/C10-30 Alkyl Acrylate Crosspolymer | | | 0.3 | 0.2 | | | | | | |
| 4-(1-Phenylethyl)-1,3-benzenediol | 4-(1-Phenylethyl)-1,3-benzenediol | 0.5 | | | | | | | | | |
| 1,2-Propylene Glycol 99P GC | Propylene Glycol | | 5.0 | | | | | | | | |
| Pseudo-ceramide 391 | N-(1-Hexadecanoyl)-4-hydroxy-L-proline (1-hexadecyl) ester | | 0.1 | | | | | 0.2 | | 0.5 | |
| Retinyl Palmitate in Oil (DSM Nutrinol Products) | Retinyl Palmitate | | | | | | | 0.2 | | | |
| Sepigel 305 | Polyacrylamide, C13-14 Isoparaffin, Laureth-7 | | | | | | | | 1.0 | | |
| Sodium Chloride | Sodium Chloride | | | | | | | | 1.0 | | |
| Sodium Hydroxide (10% sol.) | Sodium Hydroxide | | 0.3 | 0.6 | 0.4 | | | | | | |
| Solubilizer 611674 (Symrise) | PEG-40 Hydrogenated Castor Oil, Trideceth-9, Water (Aqua) | | | | | | | | | | 2.0 |

TABLE 1-continued

| RAW MATERIAL NAME (MANUFACTURER) | INCI | \% BY WEIGHT | | | | | | | | | |
|---|---|---|---|---|---|---|---|---|---|---|---|
| | | 1 | 2 | 3 | 4 | 5 | 6 | 7 | 8 | 9 | 10 |
| Sun Flower Oil (Wagner) | Helianthus Annuus (Sunflower) Seed Oil | | | | | | 5.0 | | | | |
| Sweet Almond Oil (Wagner) | Prunus dulcis | | | | | | 5.0 | | | | |
| SymMatrix (Symrise) | Maltodextrin, Rubus Fruticosus (Blackberry) Leaf Extract | | 0.1 | | | 0.3 | 1.0 | | | | |
| Symdiol 68 (Symrise) | 1,2-Hexanediol, Caprylylglycol | 0.5 | | | | | | | | | |
| Symrise Fragrance | Fragrance | 0.3 | 0.3 | 0.3 | 0.2 | 0.4 | 0.4 | 0.5 | 0.3 | 0.3 | 1.0 |
| Tamasterol (Tama Biochemicals) | Phytosterols | | | | | | | | | 0.3 | |
| Tego Betain L7 (Degussa) | Cocamidopropyl Betaine | | | | | | 6.0 | | | | |
| Tegosoft PC 31(Degussa) | | | | | | | | | | 0.3 | |
| Tegosoft TN (Degussa) | C12-15 Alkyl Benzoate | | | 5.0 | | 5.0 | | | | | |
| Triethanolamine, 99% | Triethanolamine | | | | | 0.5 | | | | | |
| Tocopherol Acetate (DSM Nutritional Products) | Tocopheryl Acetate | | | 0.5 | | 0.5 | 3.0 | | | 0.3 | |
| Zirkonal L 450 (BK Giulini) | Aluminium Zirconium Pentachloro-hydrate (40% aqueous solution) | | | | | | | | | | 37.0 |
| Water, demineralized | Water (Aqua) | to 100 | to 100 | to 100 | to 100 | to 100 | to 100 | to 100 | to 100 | to 100 | to 100 |

EXAMPLE 11

Comparison of the Reduction in Reddening by Ginger Extract (Active Compound A, not According to the Invention), Bisabolol (Active Compound B, not According to the Invention) and a Mixture of Bisabolol and Ginger Extract (Active Compound Combination C, According to the Invention) in an SDS Irritation Study Procedure:

The SDS inflammation test was used as the test model. The study was conducted on the inside under-arm of 20 subjects (9 female, 11 male, age: 24-62 years). The reddening of the skin was recorded with a Minolta-Chromameter CR 300 via the a* value of the La'b' colour system, which describes the position on the red-green axis. The measurements were taken before and 4-6 hours after raising the erythema by 24-hour occlusive treatment with SDS (sodium dodecyl sulfate). The skin was then treated with the test formulation in question 2 times daily for 3 days. 4-6 h after the last application on day 3, the reddening of the skin was determined and the reduction in reddening was calculated from this.

Formulation:

For the study, a defined amount of the active compound combination C according to the invention was incorporated into an O/W emulsion. For comparison purposes, the comparison active compounds A and B were incorporated into separate O/W emulsions.

Extrapon Ginger (Symrise) comprising 1% of ginger $CO_2$ extract, characterized by 25-33% in total of piquant substances with gingerols, shogaols (<3%) and zingerone (<0.5%) and 38-46% of steam-volatile constituents was employed as comparison active compound A.

TABLE 2

Composition of the formulations (data in wt. %):

| Raw material name (Manufacturer) | INCI | Placebo | Ginger extract (active compound A) | Bisabolol (active compound B) | Ginger extract/ bisabolol (active compound combination C) |
|---|---|---|---|---|---|
| -(-Alpha-)-Bisabolol, natural (Symrise) | Bisabolol | \ | \ | 0.1 | 0.05 |

TABLE 2-continued

Composition of the formulations (data in wt. %):

| Raw material name (Manufacturer) | INCI | Placebo | Ginger extract (active compound A) | Bisabolol (active compound B) | Ginger extract/ bisabolol (active compound combination C) |
|---|---|---|---|---|---|
| Extrapon Ginger (Symrise) | Water (Aqua), Butylene Glycol, *Zingiber Officinale* (Ginger) Root Extract, PEG-40 Hydrogenated Castor Oil, Trideceth-9 | \ | 0.1* | \ | 0.05** |
| Dracorin CE (Symrise) | Glyceryl Stearate Citrate | 1.5 | 1.5 | 1.5 | 1.5 |
| Emulsiphos (Symrise) | Potassium Cetyl Phosphate Hydrogenated Palm Glyceride | 2.0 | 2.0 | 2.0 | 2.0 |
| Dracorin GMS (Symrise) | Glyceryl Stearate | 3.5 | 3.5 | 3.5 | 3.5 |
| Neutral oil | Caprylic/Capric Triglyceride | 10.0 | 10.0 | 10.0 | 10.0 |
| Dragocid Liquid (Symrise) | Phenoxyethanol, Methyl-, Ethyl-, Propyl, Butyl-, Isobutylparaben | 0.1 | 0.1 | 0.1 | 0.1 |
| NaOH solution, 10% | Sodium Hydroxide | 0.1 | 0.1 | 0.1 | 0.1 |
| Water | Water | to 100 | to 100 | to 100 | to 100 | pH: 6.0
*0.1 wt. % of Extrapon Ginger (Symrise) comprising 0.001 wt. % of ginger extract
**0.05 wt. % of Extrapon Ginger (Symrise) comprising 0.0005 wt. % of ginger extract Result:

The results of the measurement of reddening (a* value) in the SDS irritation study on the active compound combination investigated, comprising the mixture C according to the invention or the comparison systems with active compound A or B, clearly show a synergistic effect of mixture C according to the invention. This test series thus shows by way of example that the active compound mixtures according to the invention have a synergistically significantly improved action compared with products A (ginger extract) and B (bisabolol).

TABLE 3

Reduction in reddening (a* value) after 3 days

| Test pattern | Reduction in reddening relative to the start conditions | Placebo-corrected reduction in reddening* |
|---|---|---|
| Formulation with active compound A | 2.27 | 0.87 |
| Formulation with active compound B | 2.42 | 1.02 |
| Formulation with active compound combination C | 2.90 | 1.50 |
| Placebo | 1.40 | |

*Placebo-corrected reduction in reddening = reduction in reddening$_{active\ compound}$ − reduction in reddening$_{placebo}$ Calculation of the synergy index (SI) value according to Kull for the reduction in reddening in the SDS inflammation test for a mixture of bisabolol and ginger extract after a treatment time of 3 days:

| | A 0.1 wt. % Extrapon Ginger* | B 0.1 wt. % Bisabolol | C 0.05 wt. % Extrapon Ginger** and 0.05% Bisabolol |
|---|---|---|---|
| Placebo-corrected reduction in reddening after 3 days | 0.87 | 1.02 | 1.50 |
| Kull's equation: SI = C × D/A + C × E/B | | | |
| A: Reduction in reddening for active compound A | 0.87 | | |
| B: Reduction in reddening for active compound B | 1.02 | | |

-continued

|  | A<br>0.1 wt. %<br>Extrapon Ginger* | B<br>0.1 wt. %<br>Bisabolol | C<br>0.05 wt. %<br>Extrapon Ginger**<br>and 0.05% Bisabolol |
|---|---|---|---|
| C: Reduction in reddening for mixture A + B | 1.50 | | |
| D: Content of A in C | 0.5 | | |
| E: Content of B in C | 0.5 | | |
| SI: Synergy index | 1.597 | | |

*0.1 wt. % of Extrapon Ginger (Symrise) comprising 0.001 wt. % of ginger extract
**0.05 wt. % of Extrapon Ginger (Symrise) comprising 0.0005 wt. % of ginger extract The calculation was performed with the aid of the literature (D. C. Steinberg, Cosmetics & Toiletries 2000, 115 (11), 59-62 and F. C. Kull et al., Applied Microbiology 1961, 9, 538-541). In contrast to the examples described there, in which decreasing values for A, B and C (such as e.g. the minimum inhibitory concentration in antimicrobial tests) mean a better activity and SI values of <1 thus demonstrate a synergistic action, increasing values in the reduction in reddening investigated here mean a better activity. According to Kull's equation, evidence of a synergy effect results from SI values of >1.

The calculated SI value of 1.597 clearly shows that the mixture is a highly synergistic combination of active compounds.

EXAMPLE 12

Comparison of the Reduction in Redness by Ginger Extract (Active Compound A, not According to the Invention), Bisabolol (Active Compound B, not According to the Invention) and a Mixture of Bisabolol and Ginger Extract (Active Compound Combination C, According to the Invention) in an SDS Irritation Study Procedure:

The SDS inflammation test was used as the test model. The study was conducted analogously to Example 11.

Formulation:

For the study, a defined amount of the active compound combination C according to the invention was incorporated into an O/W emulsion. For comparison purposes, the comparison active compounds A and B were incorporated into separate O/W emulsions.

TABLE 4

Composition of the formulations (data in wt. %):

| Raw material name (Manufacturer) | INCI | Placebo | Ginger extract (active compound A) | Bisabolol (active compound B) | Ginger extract/ bisabolol (active compound combination C) |
|---|---|---|---|---|---|
| -(-Alpha-)- Bisabolol, natural (Symrise) | Bisabolol | \ | \ | 0.1 | 0.05 |
| Ginger CO$_2$ Extract (Flavex) | Zingiber Officinale (Ginger) Root Extract | \ | 0.001 | \ | 0.0005 |
| Dracorin CE (Symrise) | Glyceryl Stearate Citrate | 1.5 | 1.5 | 1.5 | 1.5 |
| Emulsiphos (Symrise) | Potassium Cetyl Phosphate Hydrogenated Palm Glyceride | 2.0 | 2.0 | 2.0 | 2.0 |
| Dracorin GMS (Symrise) | Glyceryl Stearate | 3.5 | 3.5 | 3.5 | 3.5 |
| Neutral oil | Caprylic/Capric Triglyceride | 10.0 | 10.0 | 10.0 | 10.0 |
| Dragocid Liquid (Symrise) | Phenoxyethanol, Methyl-, Ethyl-, Propyl, Butyl-, Isobutylparaben | 0.1 | 0.1 | 0.1 | 0.1 |
| NaOH solution, 10% | Sodium Hydroxide | 0.1 | 0.1 | 0.1 | 0.1 |
| Water | Water | to 100 | to 100 | to 100 | to 100 | pH: 6.0

The ginger extract used was a $CO_2$ extract which is characterized by a total content of 25-33% of piquant substances with gingerols, shogaols (<3%) and zingerone (<0.5%) and 38-46% of steam-volatile constituents.

The results in the investigation of the reduction in reddening substantially corresponded to those of Example 11.

EXAMPLES F1-F8

Oral Hygiene Products

A mixture S comprising 99 wt. % (−)-alpha-bisabolol and 1 wt. % ginger extract (comprising 18.8% [6]-gingerol, 3.9% [8]-gingerol and 5.3% [10]-gingerol) was employed in Examples F1-F8.

F1: Gel dental cream having an activity against bad breath

|  | I (%) | II (%) | III (%) |
| --- | --- | --- | --- |
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Peppermint aroma | 1.00 | 1.00 | 1.00 |
| Mixture S | 0.025 | 0.06 | 0.12 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Dist. water | to 100.00 | to 100.00 | to 100.00 |

F2: Dental cream against plaque having an activity against bad breath

|  | I (%) | II (%) | III (%) |
| --- | --- | --- | --- |
| Carrageenan | 0.90 | 0.90 | 0.90 |
| Glycerin | 15.00 | 15.00 | 15.00 |
| Sorbitol 70%, in water | 25.00 | 25.00 | 25.00 |
| PEG 1000 | 3.00 | 3.00 | 3.00 |
| Na fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccharinate | 0.40 | 0.40 | 0.40 |
| Precipitated silica | 20.00 | 20.00 | 20.00 |
| Titanium dioxide | 1.00 | 1.00 | 1.00 |
| PHB methyl ester | 0.10 | 0.10 | 0.10 |
| Spearmint aroma | 1.10 | 1.10 | 1.10 |
| Mixture S | 0.03 | 0.07 | 0.14 |
| Sodium dodecyl sulfate | 1.30 | 1.30 | 1.30 |
| Dist. water | to 100.00 | to 100.00 | to 100.00 |

F3: Dental cream against sensitive teeth having an activity against bad breath

|  | I (%) | II (%) | III (%) |
| --- | --- | --- | --- |
| Na carboxymethylcellulose | 0.70 | 0.70 | 0.70 |
| Xanthan gum | 0.50 | 0.50 | 0.50 |
| Glycerin | 15.00 | 15.00 | 15.00 |
| Sorbitol 70%, in water | 12.00 | 12.00 | 12.00 |
| K nitrate | 5.00 | 5.00 | 5.00 |
| Na monofluorophosphate | 0.80 | 0.80 | 0.80 |
| PHB methyl ester | 0.15 | 0.15 | 0.15 |
| PHB propyl ester | 0.05 | 0.05 | 0.05 |
| Na saccharinate | 0.20 | 0.20 | 0.20 |
| Eucalyptus/menthol aroma | 1.00 | 1.00 | 1.00 |
| Mixture S | 0.025 | 0.06 | 0.14 |
| Ca carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Dist. water | to 100.00 | to 100.00 | to 100.00 |

F4: Ready-to-use mouthwash with fluoride having an activity against bad breath

|  | I (%) | II (%) | III (%) |
| --- | --- | --- | --- |
| Ethanol | 7.00 | 7.00 | 7.00 |
| Glycerin | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Cinnamon/menthol aroma | 0.15 | 0.15 | 0.15 |
| Mixture S | 0.01 | 0.02 | 0.03 |
| Dyestuff | 0.01 | 0.01 | 0.01 |
| Dist. water | to 100.00 | to 100.00 | to 100.00 |

F5: Mouthwash concentrate having an activity against bad breath

|  | I (%) | II (%) | III (%) |
| --- | --- | --- | --- |
| Ethanol, 95% strength | 80.00 | 80.00 | 80.00 |
| Na cyclamate | 0.15 | 0.15 | 0.15 |
| *Eucalyptus*/wintergreen aroma | 3.50 | 3.50 | 3.50 |
| Dyestuff | 0.01 | 0.01 | 0.01 |
| Mixture S | 0.50 | 1.00 | 3.00 |
| Dist. water | to 100.00 | to 100.00 | to 100.00 |

F6: Chewing gum against bad breath

|  | I (%) | II (%) | III (%) |
| --- | --- | --- | --- |
| Chewing gum base | 21.00 | 21.00 | 21.00 |
| Glucose syrup | 16.50 | 16.50 | 16.50 |
| Glycerin | 0.50 | 0.50 | 0.50 |
| Powdered sugar | 60.45 | 60.36 | 60.27 |
| Spearmint aroma | 1.50 | 1.50 | 1.50 |
| Mixture S | 0.05 | 0.14 | 0.23 |

F7: Sugar-free chewing gum against bad breath

|  | I (%) | II (%) | III (%) |
| --- | --- | --- | --- |
| Chewing gum base | 30.00 | 30.00 | 30.00 |
| Sorbitol, powder | 38.45 | 38.40 | 38.30 |
| Palatinite | 9.50 | 9.50 | 9.50 |
| Xylitol | 2.00 | 2.00 | 2.00 |

-continued

F7: Sugar-free chewing gum against bad breath

|  | I (%) | II (%) | III (%) |
|---|---|---|---|
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerin | 1.00 | 1.00 | 1.00 |
| Cinnamon/menthol aroma | 1.50 | 1.50 | 1.50 |
| Mixture S | 0.05 | 0.10 | 0.20 |

F8: Gelatine capsules against bad breath for direct consumption

|  | I (%) | II (%) | III (%) |
|---|---|---|---|
| Gelatine shell: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core composition: | | | |
| Plant oil triglyceride | 82.00 | 74.00 | 60.00 |
| Aroma B | 7.85 | 15.50 | 28.50 |
| Mixture S | 0.15 | 0.50 | 1.50 |

Aroma B here had the following composition (data in each case in wt. %):

0.1% neotame powder, 0.05% aspartame, 29.3% peppermint oil arvensis, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, had a diameter of 5 mm, and the weight ratio of core material to shell material was 90:10. The capsules opened in the mouth within less than 10 seconds and dissolved completely within less than 50 seconds.

The invention claimed is:

1. A skin irritation-reducing cosmetic formulation having skin-irritation reducing action comprising:
   i) bisabolol; and
   ii) (a) a ginger extract containing a compound selected from the group consisting of: gingerols, gingerdiols, shogaols, gingerdios, dehydrogingerdiones or paradols; or
   (b) a compound obtained from a separation of a ginger extract, wherein the compound is selected chosen from the group consisting of: gingerols, shogaols, gingerdiols, dehydrogingerdiones, paradols or a mixture thereof; wherein the weight ratio of component i) to component ii) is 100,000:1 to 10:1 and the skin irritation-reducing action of the combination of components i) and ii) is increased synergistically relative to the skin irritation-reducing action of components i) and ii) individually.

2. The cosmetic formulation of claim 1, wherein components i) and ii) each individually have skin irritation-reducing action.

3. The cosmetic formulation of claim 1, wherein component ii) is a ginger extract.

4. The cosmetic formulation of claim 1, wherein the sum of components i) and ii) is at least 90 wt %, based upon the total weight of the formulation or component i) is present in an amount of 90-99.999 wt %, based upon the total weight of the formulation or component ii) is present in an amount of 0.001-10 wt %, based upon the total weight of the formulation.

5. A medicament for treating skin irritation, comprising the cosmetic formulation of claim 1.

6. A kit comprising the cosmetic formulation of claim 1.

7. The cosmetic formulation of claim 1, wherein the formulation is a liquid formulation.

8. The liquid formulation of claim 7 comprising oil as a solvent.

9. The cosmetic formulation of claim 1, wherein the formulation is a solid formulation.

10. The cosmetic formulation of claim 1, wherein the weight ratio of component i) to component ii) is 1,000:1 to 50:1.

11. The cosmetic formulation of claim 4, wherein the sum of components i) and ii) is at least 90 wt %, based upon the total weight of the formulation.

12. The cosmetic formulation of claim 4, wherein component i) is present in an amount of 90-99.999 wt %, based upon the total weight of the formulation.

13. The cosmetic formulation of claim 4, wherein component ii) is present in an amount of 0.001-10 wt %, based upon the total weight of the formulation.

* * * * *